US009509963B2

(12) United States Patent  
Enjouji

(10) Patent No.: US 9,509,963 B2  
(45) Date of Patent: Nov. 29, 2016

(54) INDEPENDENT WIRELESS DIALYSIS INSTRUMENT MONITORING SYSTEM AND METHOD USING CAMERA WITH PROGRAMMABLE CAMERA CONTROL MECHANISM

(71) Applicant: I. T. I. CO., LTD., Nagasaki-shi, Nagasaki (JP)

(72) Inventor: Takashi Enjouji, Fukuoka (JP)

(73) Assignee: I. T. I. CO., LTD., Nagasaki-shi (JP)

( * ) Notice: Subject to any disclaimer, the term of this patent is extended or adjusted under 35 U.S.C. 154(b) by 223 days.

(21) Appl. No.: 13/863,483

(22) Filed: Apr. 16, 2013

(65) Prior Publication Data

US 2013/0270160 A1   Oct. 17, 2013

(30) Foreign Application Priority Data

Apr. 16, 2012   (JP) ................................ 2012-093236

(51) Int. Cl.
```
B01D 61/00        (2006.01)
C02F 1/44         (2006.01)
```
(Continued)

(52) U.S. Cl.
CPC ............... *H04N 7/183* (2013.01); *A61M 1/14* (2013.01); *A61M 1/1656* (2013.01); *G06F 19/3418* (2013.01); *A61M 2205/3584* (2013.01)

(58) Field of Classification Search
CPC ..... A61B 5/0031; A61K 33/14; A61M 1/16; A61M 1/1656; A61M 1/3643; A61M 2001/165; A61M 2001/3437; A61M 2001/1609; A61M 2001/1666; A61N 1/00; A61N 1/08; A61N 1/37223; A61N 1/37229; A61N 1/37252; B01D 61/00; B01D 61/08; B01D 61/12; B01D 61/26; B01D 61/28; B01D 61/32; C02F 1/32; C02F 1/283; C02F 1/441; C02F 9/00
USPC ....... 210/85, 90, 96.2, 97, 143, 252, 321.71, 210/418, 420, 646, 647; 604/4, 65, 66; 607/60; 709/217
See application file for complete search history.

(56) References Cited

U.S. PATENT DOCUMENTS 5,961,446 A * 10/1999 Beller et al. .................. 600/300  
6,251,437 B1 * 6/2001 Fischbach ..................... 424/489

(Continued)

FOREIGN PATENT DOCUMENTS

JP   2001-346870 A   12/2001  
JP   2001-353214 A   12/2001

(Continued)

OTHER PUBLICATIONS

The FreeDictionary.com—Definitions of Image [accessed Jan. 8, 2014; 10 pages].*

(Continued)

*Primary Examiner* — Dirk Bass  
*Assistant Examiner* — Hayden Brewster  
(74) *Attorney, Agent, or Firm* — Typha IP LLC

(57) ABSTRACT

Provided is a dialysis treatment instrument monitoring system capable of communicating with an extrahospital terminal via the Internet without affecting an intrahospital network. In the hospital equipped with a dialysis treatment instrument monitoring system monitoring dialysis treatment instruments including a dialysate feeding device, a bulk powder dissolving device, and a RO device, while a staff is absent in the hospital, the dialysate feeding device and the bulk powder dissolving device perform a dialysis preparation processing of cleaning and sterilizing inside the devices, and stop if an error occurs during execution of the dialysis preparation processing. If an error occurs in any of the dialysis treatment instruments, a network camera takes an image of a display of the dialysis treatment instrument in which the error occurred, and transmits image data to the terminal on the Internet via a mobile router dedicated to the dialysis treatment instrument monitoring system.

12 Claims, 18 Drawing Sheets

(51) Int. Cl.
*H04N 7/18* (2006.01)
*A61M 1/14* (2006.01)
*G06F 19/00* (2011.01)
*A61M 1/16* (2006.01)

(56) References Cited

U.S. PATENT DOCUMENTS

| | | |
|---|---|---|
| 2003/0105435 A1* | 6/2003 | Taylor .................... 604/252 |
| 2004/0211718 A1* | 10/2004 | Deguchi et al. ............ 210/252 |
| 2005/0137653 A1 | 6/2005 | Friedman et al. |
| 2007/0135866 A1* | 6/2007 | Baker et al. ................. 607/60 |
| 2009/0080757 A1* | 3/2009 | Roger ............... A61M 1/3653 382/134 |
| 2012/0011253 A1 | 1/2012 | Friedman et al. |
| 2012/0138533 A1* | 6/2012 | Curtis et al. .............. 210/646 |
| 2013/0018355 A1* | 1/2013 | Brand et al. .............. 604/500 |

FOREIGN PATENT DOCUMENTS

| | | |
|---|---|---|
| JP | 2005-027798 A | 2/2005 |
| JP | 2007-526024 A | 9/2007 |
| JP | 2008-054265 A | 3/2008 |
| JP | 2010-279423 A | 12/2010 |
| JP | 2011-029898 A | 2/2011 |
| JP | 2011-228919 A | 11/2011 |
| WO | 2005-057466 A | 6/2005 |
| WO | 2010/106614 A | 9/2010 |

OTHER PUBLICATIONS

Office Action issued by Japanese Patent Office dated on Feb. 23, 2016 for corresponding Japanese Patent Application No. 2012-093236.
Japanese Office Action mailed on Sep. 6, 2016 for corresponding Japanese Patent Application No. 2012-093236 with machine translation.

* cited by examiner

FIG.12

| |
|---|
| IMAGE DATA |
| ⋮ |
| REGISTERED E-MAIL ADDRESS 1 |
| REGISTERED E-MAIL ADDRESS 2 |
| REGISTERED E-MAIL ADDRESS 3 |
| REGISTERED E-MAIL ADDRESS 4 |
| ⋮ |
| PRESET POSITION INFORMATION 1 |
| PRESET POSITION INFORMATION 2 |
| PRESET POSITION INFORMATION 3 |
| ⋮ |
| CAMERA OPERATING PROGRAM |
| ERRONEOUS DEVICE IMAGING PROGRAM |
| E-MAIL TRANSMISSION PROGRAM |
| ⋮ |
| OTHER DATA |

32b

INDEPENDENT WIRELESS DIALYSIS INSTRUMENT MONITORING SYSTEM AND METHOD USING CAMERA WITH PROGRAMMABLE CAMERA CONTROL MECHANISM

CROSS REFERENCE TO RELATED APPLICATIONS

This application claims priority under 35 U.S.C. §119(a) on patent application JP 2012-093236 filed on Apr. 16, 2012, the entire contents of which are incorporated herein by reference.

FIELD OF THE INVENTION

The present invention relates to a dialysis treatment instrument monitoring system and a dialysis treatment instrument monitoring method, and specifically to the system and method for monitoring a dialysis treatment instrument during a time period when an operator of the dialysis treatment instrument is absent in a facility such as nighttime and holiday.

RELATED ART

When a dialysis treatment is performed on a patient in a facility such as a hospital, a plurality of medical instruments are generally operated in the facility to perform respective processing. Such dialysis treatment instruments include a refining device that refines raw water with a reverse osmosis membrane, a dissolving device that dissolves bulk powder of dialysate, and a dialysate feeding device that mixes refined water refined by the refining device with undiluted dialysate obtained by the dissolving device dissolving the bulk powder and thereby delivers dialysate. While these instruments perform processing for actually administering the dialysis treatment to a patient during the daytime when its operator is present, they perform preparation processing such as cleaning and sterilizing inside the instruments for the dialysis treatment on the following business day during nighttime and holiday when the operator is absent in the facility.

Although the dialysis treatment instrument configured as above operates to complete the above preparation processing during the time period when the operator is absent, should an error occur during execution of the preparation processing, the preparation processing may be interrupted. Because such a case may cause a problem to the dialysis treatment on the following business day, it is necessary to alert the operator as soon as possible in the case of error during execution of the preparation processing. For this reason, there is sometimes introduced into a facility such as a hospital a monitoring system that monitors an operating condition of the dialysis treatment instrument during the time period when the operator is absent and alerts the operator in the case where any failure occurs.

Some of the above monitoring systems monitor conditions of a plurality of medical instruments via a wired or wireless network, which enables remotely monitoring respective operating conditions of a plurality of medical instruments. Especially if respective operating conditions of a plurality of medical instruments are remotely monitored using a server and the server communicates with a client through an external communication network such as the Internet like the monitoring system described in Patent Document 1, it is possible to notify a person outside of the operating condition of each medical instrument.

PATENT DOCUMENT

Patent Document 1: JP 2007-526024 A

DISCLOSURE OF THE INVENTION

Problems to be Solved by the Invention

In order to introduce a new monitoring system connectable to an external communication network, a measure should be taken so that an existing information network configured by communication instruments in the same facility as the monitoring system should not be adversely affected. For example, in order to adapt a communication network connectable to an external communication network that is already embedded in the facility into the monitoring system, there can be a problem in terms of security, and the configuration of the communication network must be investigated before introducing the system, which takes time and effort.

So, the present invention was made in view of the above problems, and an object thereof is to provide a dialysis treatment instrument monitoring system capable of communicating with a terminal outside facility via an external communication network without affecting a communication network configured by other instruments in the facility.

Another object of the present invention is to provide a dialysis treatment instrument monitoring method that enables to communicate with a terminal outside a facility via an external communication network without affecting a communication network configured by other instruments in the facility.

Means for Solving the Problems

According to a dialysis treatment instrument monitoring system of the present invention, the above-described problems are solved by a dialysis treatment instrument monitoring system monitoring each of a plurality of dialysis treatment instruments operable to perform a dialysis treatment on a patient in a facility during a time period when an operator of the dialysis treatment instruments is absent in the facility, the dialysis treatment instrument monitoring system including: an imaging device taking an image of an indicator indicative of information on an operating condition of the dialysis treatment instruments; a control mechanism controlling the imaging device to selectively take an image of the indicator of any dialysis treatment instrument among the indicators mounted on each dialysis treatment instrument; a data transmission unit acquiring image data indicative of an image taken by the imaging device and transmitting the image data; and a relay instrument establishing a connection with an external communication network when the data transmission unit transmits the image data to a terminal outside the facility connected to the external communication network, in which: the plurality of dialysis treatment instruments monitored by the dialysis treatment instrument monitoring system include a refining device refining raw water with a reverse osmosis membrane, a dissolving device dissolving bulk powder of dialysate, and a dialysate feeding device mixing refined water obtained by the refining device refining the raw water with undiluted dialysate obtained by the dissolving device dissolving the bulk powder and thereby delivering the dialysate, during the time period, among the dialysis treatment instruments, the dissolving device and the dialysate feeding device perform a dialysis preparation processing of cleaning and sterilizing inside the devices and stop the dialysis preparation processing when the operating condition is turned into an abnormal condition during execution of the dialysis preparation processing, during the time period, if the operating condition of any one of the refining device, the dissolving device, and the dialysate feeding device turns into an abnormal condition, the control mechanism controls the imaging device after identifying the dialysis treatment instrument of which operating condition is turned into an abnormal condition, the imaging device selectively images the indicator of the dialysis treatment instrument identified by the control mechanism, and the data transmission unit transmits the image data indicative of the image of the indicator taken by the imaging device to the terminal via the relay instrument, and the relay instrument is provided as a device dedicated to the dialysis treatment instrument monitoring system in the facility and connected to the external communication network via a wireless communication line.

With the above dialysis treatment instrument monitoring system, during the time period when the operator of the dialysis treatment instrument is absent in the facility, if a failure occurs to any one of the refining device, the dissolving device, and the dialysate feeding device, an image of the indicator indicative of the information on the operating condition of the dialysis treatment instrument in an abnormal condition is taken and image data indicative of the image is transmitted to the terminal on the external communication network. This makes it possible to monitor the operating condition of each dialysis treatment instrument when the operator is absent, and to monitor whether the dialysis preparation processing is being correctly performed especially in the dissolving device and the dialysate feeding device.

Furthermore, with the above dialysis treatment instrument monitoring system, when the image data is transmitted to the terminal outside the facility via the external communication network, the relay instrument provided as a device dedicated to the dialysis treatment instrument monitoring system is connected to the external communication network via the wireless communication line. Namely, the dialysis treatment instrument monitoring system according to the present invention is in a state of being isolated from the communication network configured by other instruments in the facility. Thus, the image data can be transmitted to the terminal on the external communication network without affecting the communication network configured by other instruments in the facility. As a result, security of the communication network configured in the facility is ensured, and the cost required for the introduction of the system can be reduced because the time and effort is not required for investigating the communication network in the facility before introducing the system.

In the above-described dialysis treatment instrument monitoring system, the dissolving device may not start dissolving the bulk powder in a state where the dialysis preparation processing is not completed, and the dialysate feeding device may not start delivering the dialysate in a state where the dialysis preparation processing is not completed.

As described above, if the dialysis preparation processing is interrupted when the dissolving device and the dialysate feeding device are in an abnormal condition, and the original processing (specifically, dissolving bulk powder or supplying dialysate) is not performed in a state where the dialysis preparation processing is not completed, then it is more important to monitor the operating condition of the dissolving device and the dialysate feeding device during the time period when the operator is absent in the facility. Thus, the dialysis treatment instrument monitoring system according to the present invention is more significant.

In the above-described dialysis treatment instrument monitoring system, the relay instrument may be a mobile router connected to the Internet as the external communication network via a mobile communication line, and the data transmission unit may transmit an e-mail to which the image data is attached to a registered terminal that is the terminal corresponding to a registered e-mail address via the mobile router.

As described above, by transmitting an e-mail to which the image data is attached to the terminal corresponding to the registered e-mail address via the mobile router, it is possible to alert the failure of the dialysis treatment instrument by means of e-mail, which is universal means, without affecting the communication network configured by other instruments in the facility.

The above-described dialysis treatment instrument monitoring system may further include a camera body as the imaging device and a network camera equipped with a camera control unit as the control mechanism controlling the camera body; in which the terminal may be capable of communicating with the network camera via the mobile router, and a global IP address assigned to the mobile router to identify the mobile router may be a static global IP address.

As described above, if the static global IP address is assigned to the mobile router, the communication is more reliable when communicating with the network camera via the mobile router.

In the above-described dialysis treatment instrument monitoring system, the data transmission unit and the mobile router may operate by receiving electric power from an uninterruptible power source provided in the facility, and in the case where the dialysis treatment instrument operates by receiving electric power from a commercial power source, if power supply from the commercial power source to the dialysis treatment instrument is interrupted, the data transmission unit may transmit an alarming e-mail acknowledging interruption of the power supply to the registered terminal via the mobile router.

As described above, if the data transmission unit and the mobile router operate by receiving electric power from the uninterruptible power source, it is possible to transmit an e-mail acknowledging the interruption of the power supply from the commercial power source to the dialysis treatment instrument, and the e-mail delivery enables the operator outside the facility to be acknowledged of the occurrence of power failure.

The above-described dialysis treatment instrument monitoring system may further include an I/O module having an input port for an abnormal signal output from the dialysis treatment instrument of which operating condition is turned into an abnormal condition and an output port for a control signal output to image the indicator of the dialysis treatment instrument that output an abnormal signal, in which the I/O module includes at least an equal to or greater number of input ports than that of the dialysis treatment instruments and at least an equal to or greater number of output ports than that of the imaging device.

As described above, the I/O module equipped with an equal to or greater number of input ports than that of the dialysis treatment instruments and an equal to or greater number of output ports than that of the imaging devices can flexibly deal with a number increase of the dialysis treatment instruments and the imaging devices.

In the above-described dialysis treatment instrument monitoring system, the refining device may output an abnormal signal at least when a water leak occurs in the refining device, when a storage volume in a water storage tank that reserves the raw water falls below a management value, and when a water pump pumping the raw water is in failure; the dissolving device may output an abnormal signal at least when a leak of the undiluted dialysate occurs to the dissolving device and when an internal temperature of a dissolution bath in which the bulk powder is dissolved rises above a management value; and the dialysate feeding device may output an abnormal signal at least when a feeding pressure for feeding the dialysate falls below a management value, when a solute concentration of the dialysate is out of a management range, and when the solute concentration of the undiluted dialysate in an undiluted solution tank that reserves the undiluted dialysate is out of a management range.

As described above, if the items to be monitored are specified for each of the refining device, the dissolving device, and the dialysate feeding device, and an abnormal signal is output in case an abnormality occurs to each item, it is then possible to carefully monitor the operating condition of each of the refining device, the dissolving device, and the dialysate feeding device.

Further, according to a dialysis treatment instrument monitoring method of the present invention, the above-described problems are solved by a dialysis treatment instrument monitoring method using a dialysis treatment instrument monitoring system monitoring each of a plurality of dialysis treatment instruments operable to perform a dialysis treatment on a patient in a facility during a time period when an operator of the dialysis treatment instruments is absent in the facility, the method including: a step at which an imaging device takes an image of an indicator indicative of information on an operating condition of the dialysis treatment instruments; a step at which a control mechanism controls the imaging device to selectively take an image of the indicator of any dialysis treatment instrument among the indicators mounted on each dialysis treatment instrument; and a step at which a data transmission unit acquires image data indicative of an image taken by the imaging device and transmits the acquired image data, in which: the plurality of dialysis treatment instruments monitored by the dialysis treatment instrument monitoring system include a refining device refining raw water with a reverse osmosis membrane, a dissolving device dissolving bulk powder of dialysate, and a dialysate feeding device mixing refined water obtained by the refining device refining the raw water with undiluted dialysate obtained by the dissolving device dissolving the bulk powder and thereby delivering the dialysate, during the time period, among the dialysis treatment instruments, the dissolving device and the dialysate feeding device perform a dialysis preparation processing of cleaning and sterilizing inside the devices and stop the dialysis preparation processing when the operating condition is turned into an abnormal condition during execution of the dialysis preparation processing, during the time period, if the operating condition of any one of the refining device, the dissolving device, and the dialysate feeding device is turned into an abnormal condition, the steps at which the control mechanism controls the imaging device, at which the imaging device takes an image of the indicator, and at which the data transmission unit transmits the image data are performed, in the step at which the control mechanism controls the imaging device, the control mechanism controls the imaging device after identifying the dialysis treatment instrument of which operating condition is turned into an abnormal condition, in the step at which the imaging device takes an image of the indicator, the imaging device selectively takes an image of the indicator of the dialysis treatment instrument identified by the control mechanism, and in the step at which the data transmission unit transmits the image data, in a state in which a relay instrument provided as a device dedicated to the dialysis treatment instrument monitoring system in the facility is connected to an external communication network via a wireless communication line, the data transmission unit transmits the image data indicative of the image of the indicator taken by the imaging device to a terminal outside the facility connected to the external communication network via the relay instrument.

In the above dialysis treatment instrument monitoring method, during the time period when the operator of the dialysis treatment instrument is absent in the facility, if a failure occurs to any one of the refining device, the dissolving device, and the dialysate feeding device, an image of the indicator indicative of the information on the operating condition of the dialysis treatment instrument in an abnormal condition is taken and the image data indicative of the image is transmitted to the terminal on the external communication network. This makes it possible to monitor the operating condition of each dialysis treatment instrument when the operator is absent, and to monitor whether the dialysis preparation processing is being correctly performed especially in the dissolving device and the dialysate feeding device.

Furthermore, in the above dialysis treatment instrument monitoring method, the image data is transmitted to the terminal outside the facility connected to the external communication network via the relay instrument in a state where the relay instrument provided as a device dedicated to the dialysis treatment instrument monitoring system is connected to the external communication network via the wireless communication line. Thus, the image data is to be transmitted to the terminal outside the facility in a state of being isolated from the communication network configured by other instruments in the facility. Therefore, the dialysis treatment instrument monitoring method enables the image data to be transmitted to the terminal outside the facility via the external communication network without affecting the communication network configured by other instruments in the facility.

Effects of the Invention

With the dialysis treatment instrument monitoring system according to the present invention, during the time period when the operator of the dialysis treatment instrument is absent in the facility, if a failure occurs to any one of the refining device, the dissolving device, and the dialysate feeding device, an image of the indicator indicative of the information on the operating condition of the dialysis treatment instrument in an abnormal condition is taken and the image data indicative of the image is transmitted to the terminal on the external communication network. This makes it possible to monitor the operating condition of each dialysis treatment instrument when the operator is absent, and to monitor whether the dialysis preparation processing is being correctly performed especially in the dissolving device and the dialysate feeding device.

Furthermore, when the image data is transmitted to the terminal outside the facility via the external communication network, the relay instrument provided as a device dedicated to the dialysis treatment instrument monitoring system is connected to the external communication network via the wireless communication line. Namely, the dialysis treatment instrument monitoring system according to the present invention is in a state of being isolated from the communication network configured by other instruments in the facility. Thus, the image data can be transmitted to the terminal on the external communication network without affecting the communication network configured by other instruments in the facility. As a result, security of the communication network configured in the facility is ensured, and the cost required for the introduction of the system can be reduced because the time and effort is not required for investigating the communication network in the facility before introducing the system.

BRIEF DESCRIPTION OF THE DRAWINGS

FIG. 12 is an explanatory diagram of data stored in a memory of a camera-side control mechanism;

DETAILED DESCRIPTION OF THE INVENTION

A dialysis treatment instrument monitoring system and a dialysis treatment instrument monitoring method according to an embodiment of the present invention (hereinafter, referred to as "the embodiment") will be described with reference to FIGS. 1 to 16.

Figure 1:
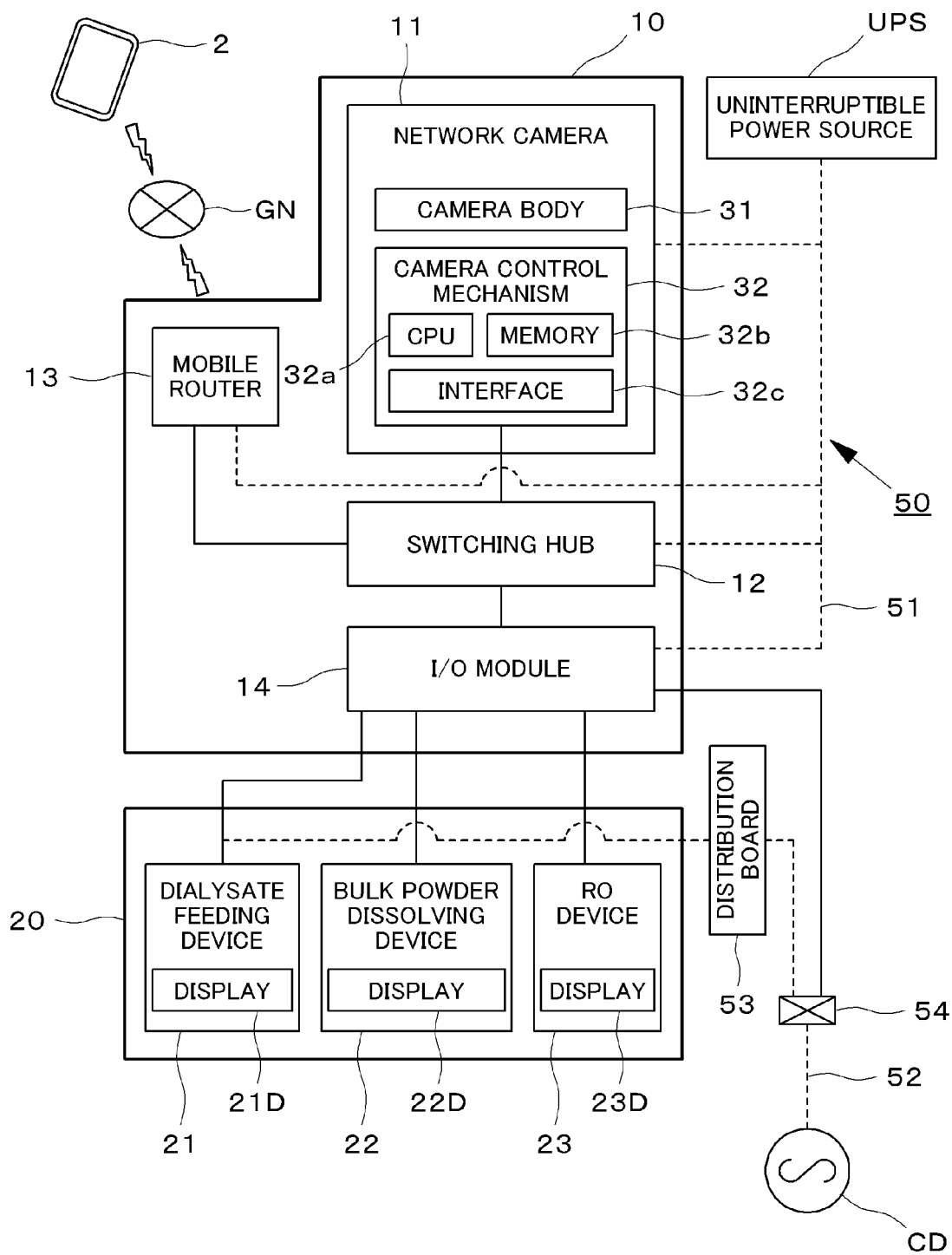
FIG. 1 is a diagram showing a configuration of a dialysis treatment instrument monitoring system according to the present invention.
Figure 2:
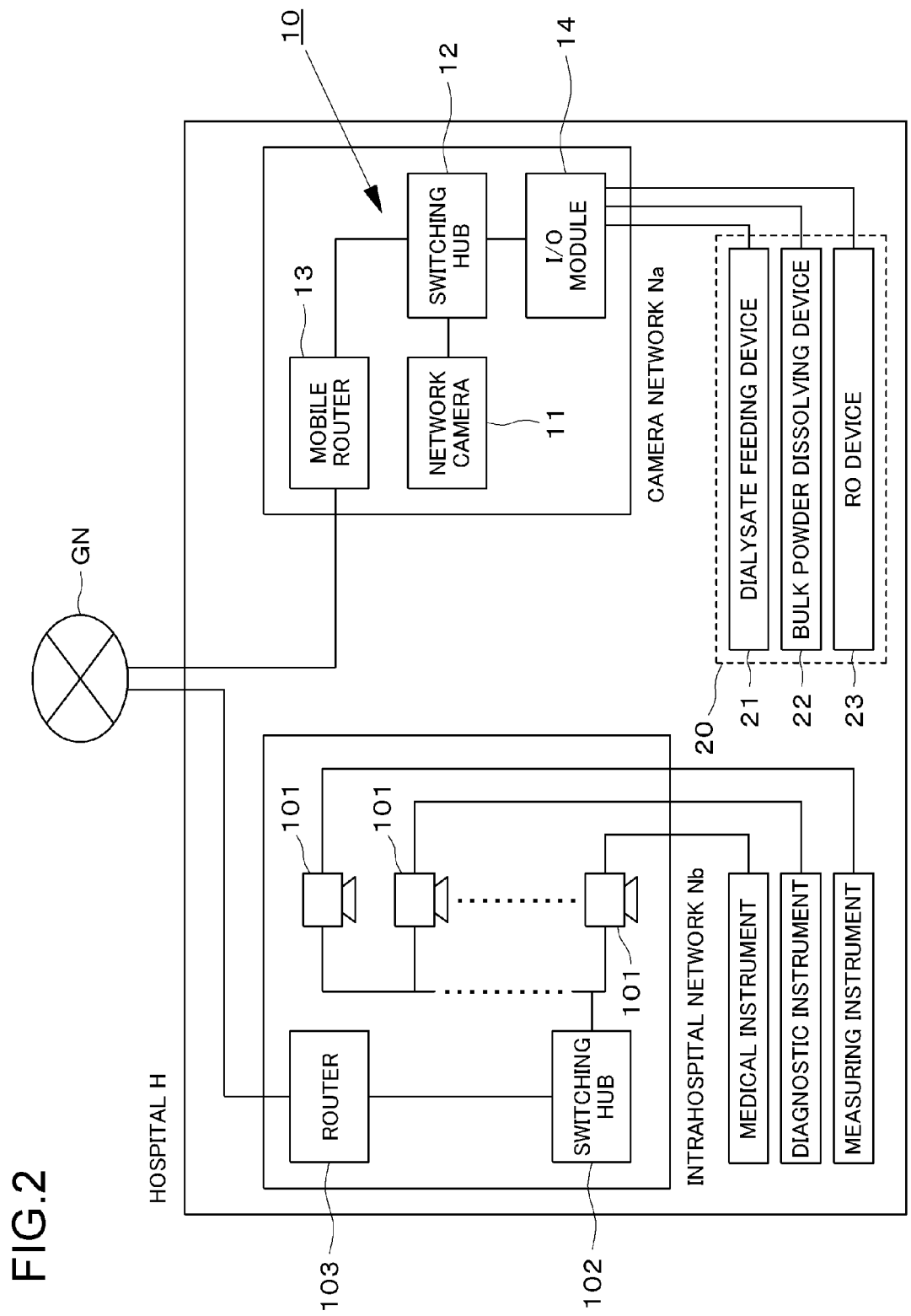
FIG. 2 is a diagram showing a communication network in a facility according to the invention.
Figure 3:
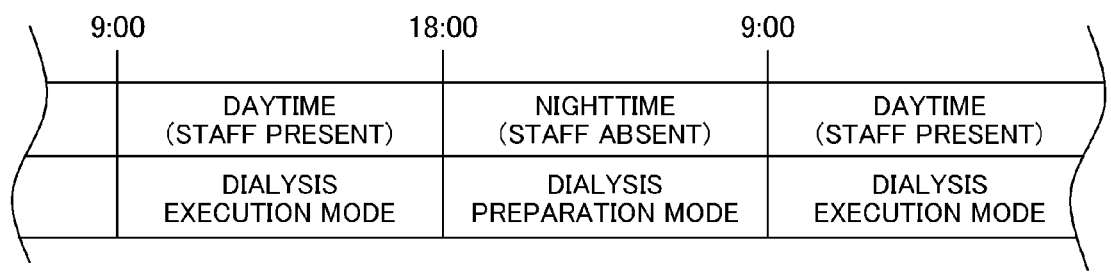
FIG. 3 is a diagram showing an operation schedule of a dialysis treatment instrument according to the invention.
Figure 4:
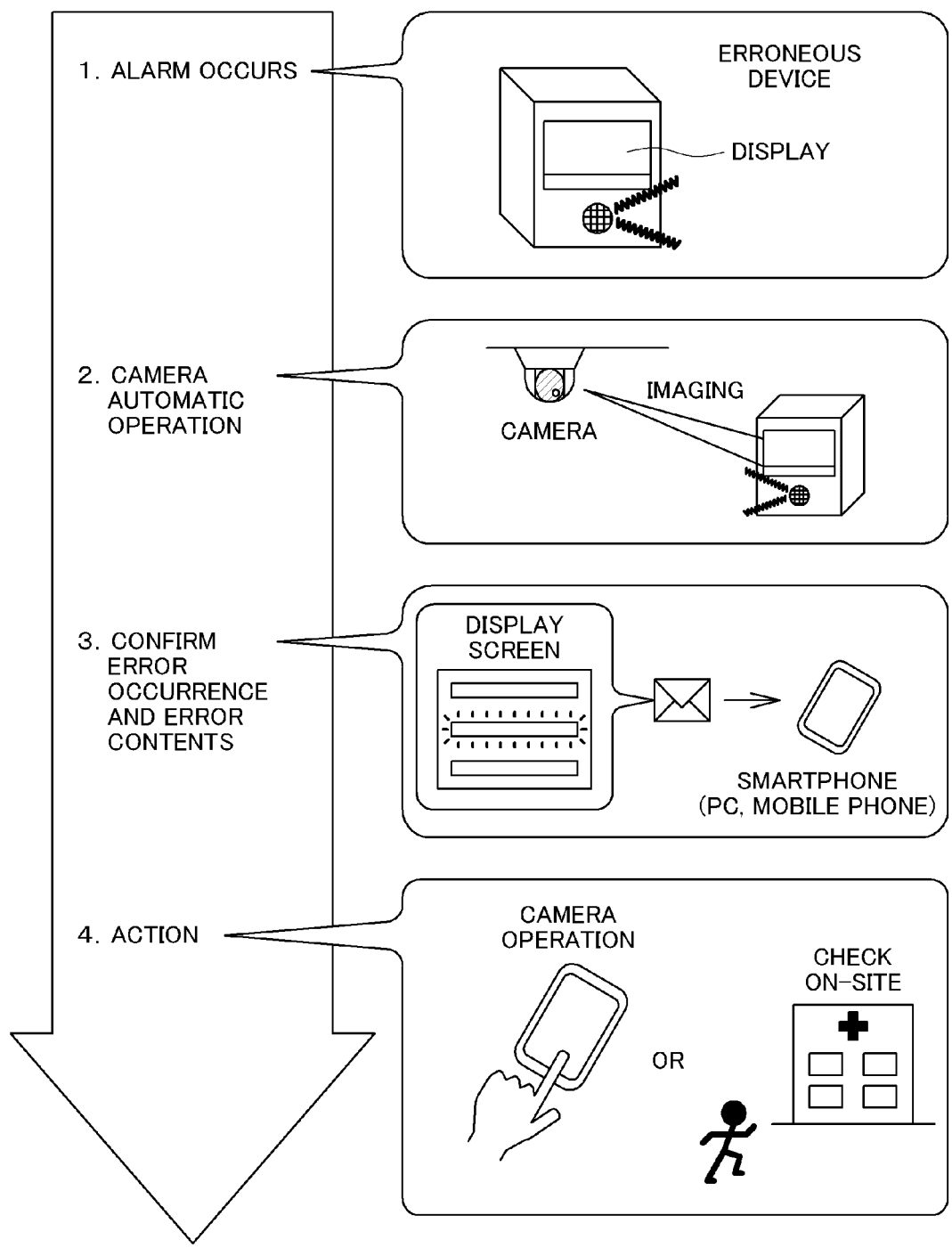
FIG. 4 is a diagram showing an operation content when an operator is absent.
Figure 5:
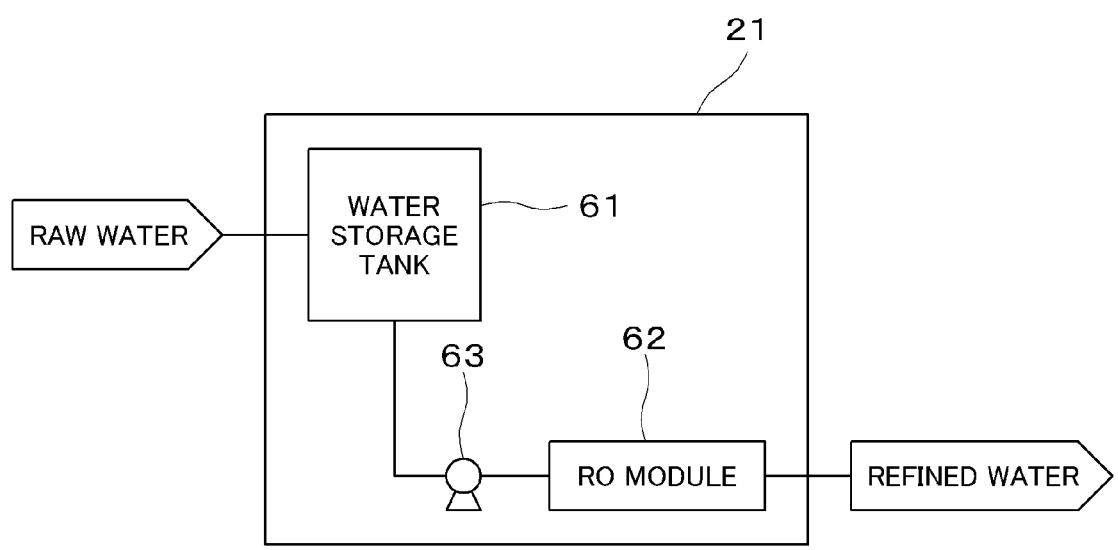
FIG. 5 is a conceptual diagram showing a configuration of a refining device according to the invention.
Figure 6:
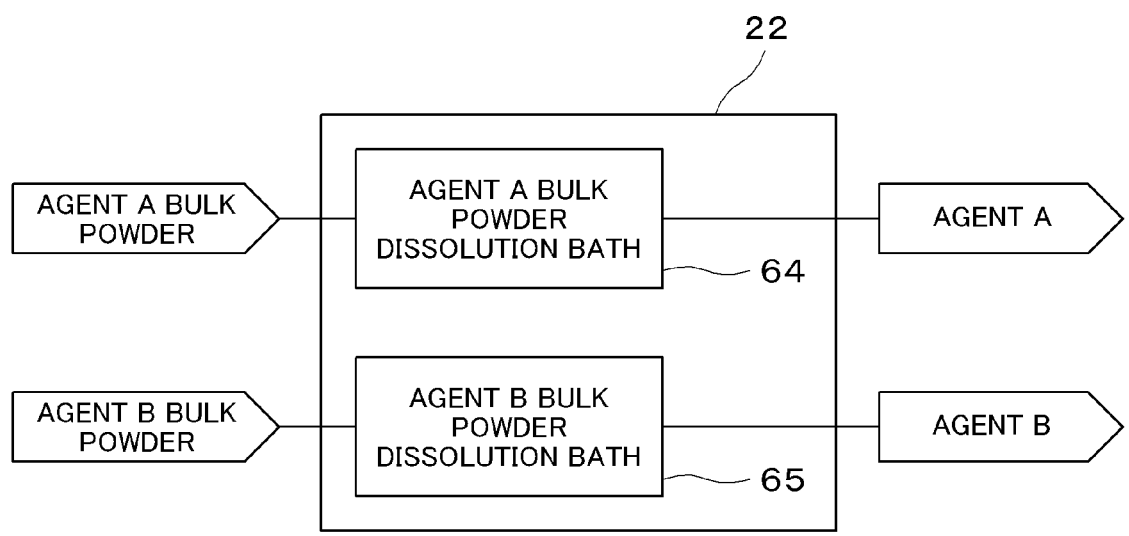
FIG. 6 is a conceptual diagram showing a configuration of a dissolving device according to the invention.
Figure 7:
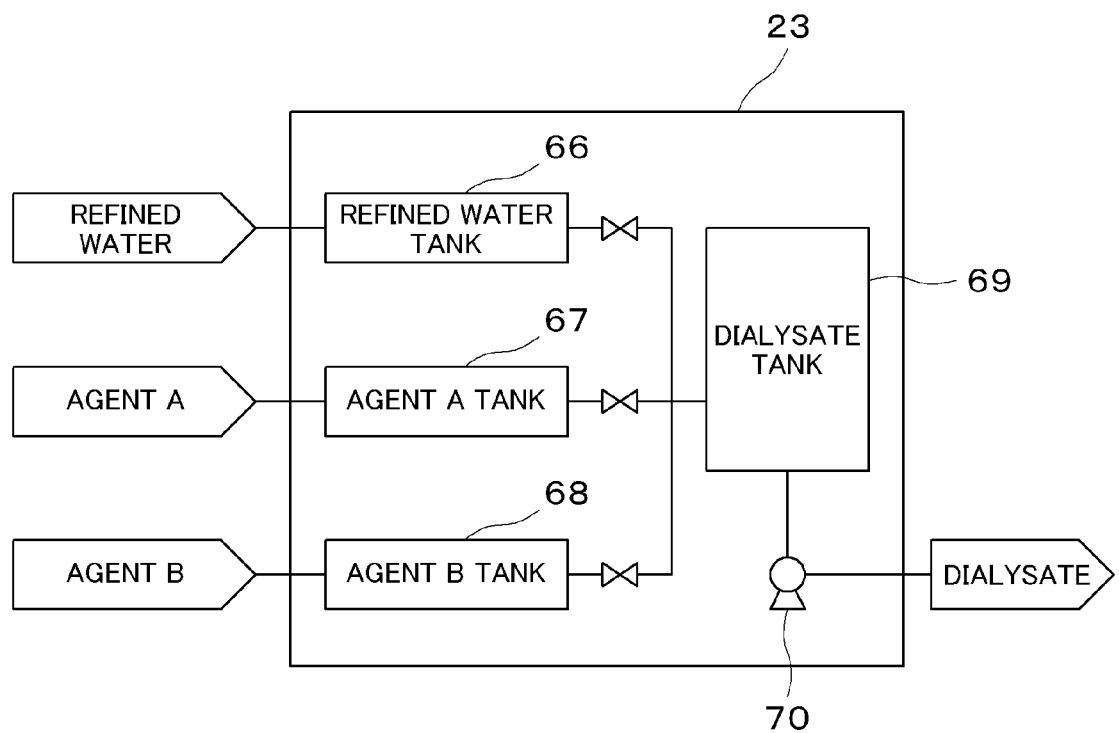
FIG. 7 is a conceptual diagram showing a configuration of a dialysate feeding device according to the invention.
Figure 8:
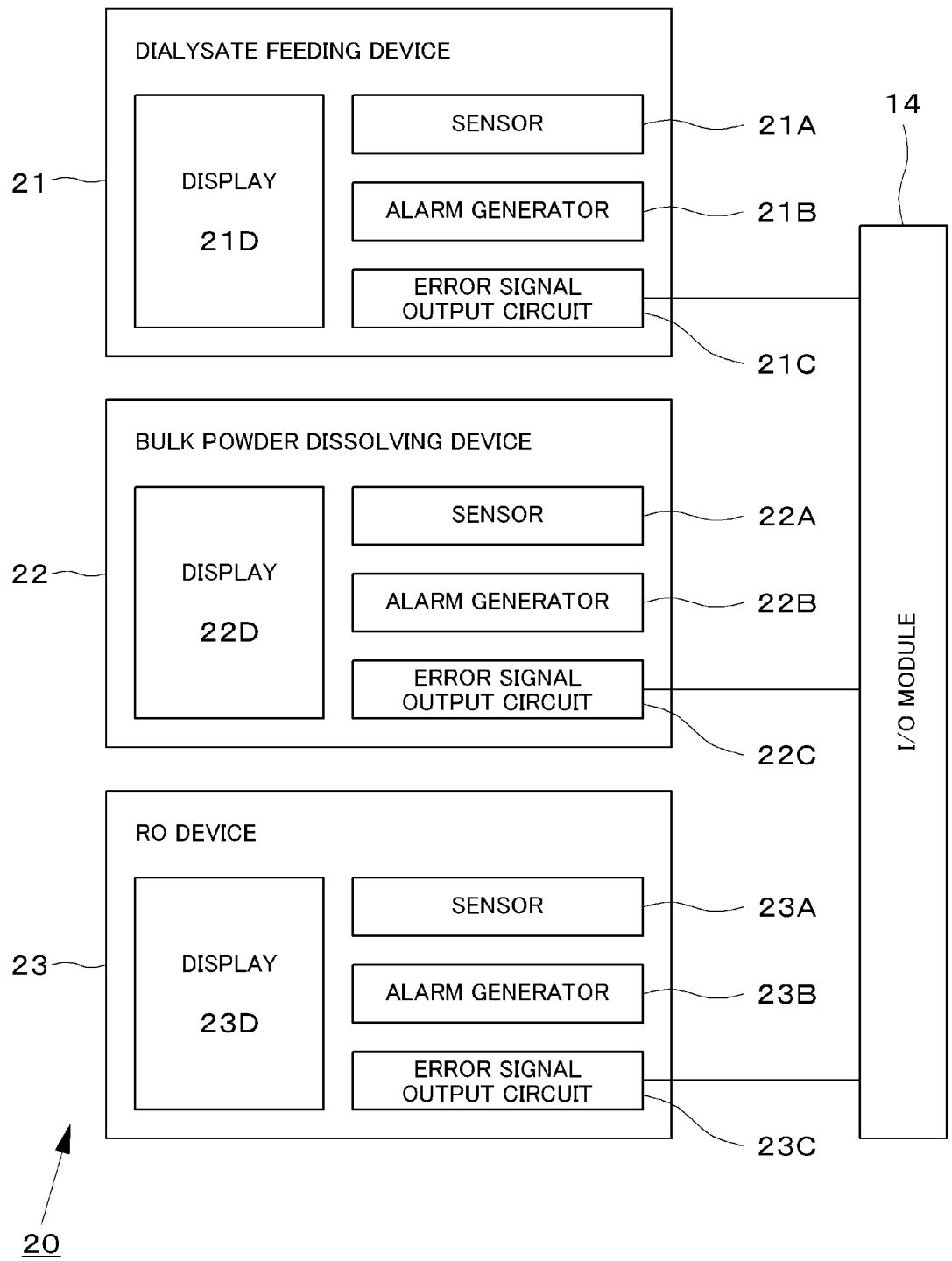
FIG. 8 is a conceptual diagram showing a measuring instrument in the dialysis treatment instrument according to the invention.
Figure 9A:
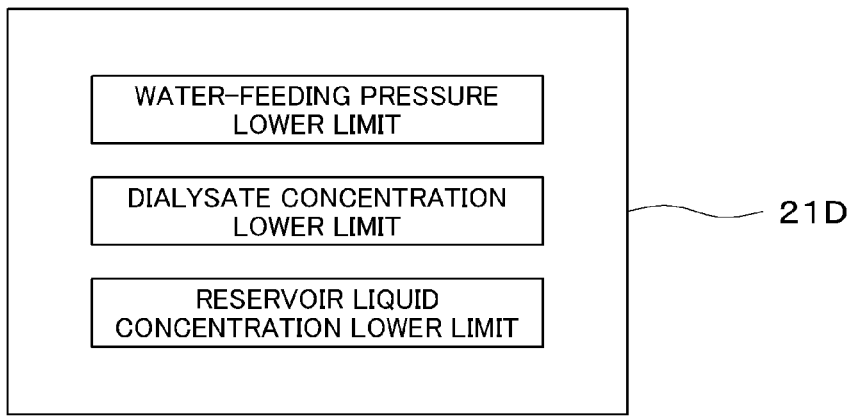
FIG. 9(A) is a diagram showing an indicator of the refining device according to the invention.
Figure 9B:
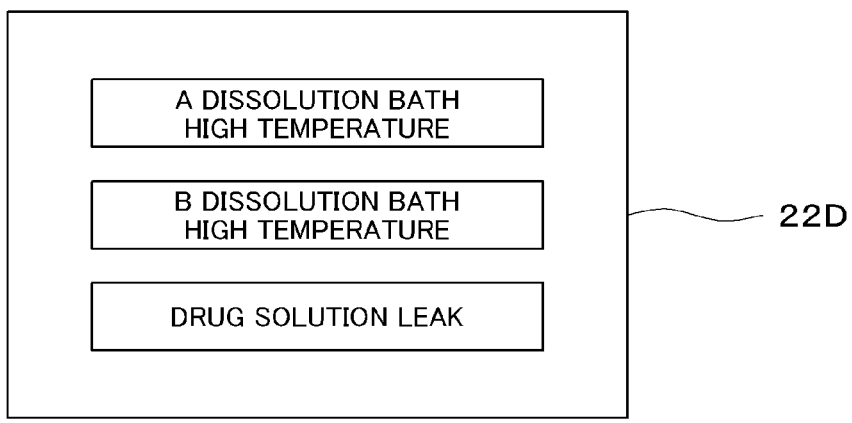
FIG. 9(B) is a diagram showing an indicator of the dissolving device according to the invention.
Figure 9C:
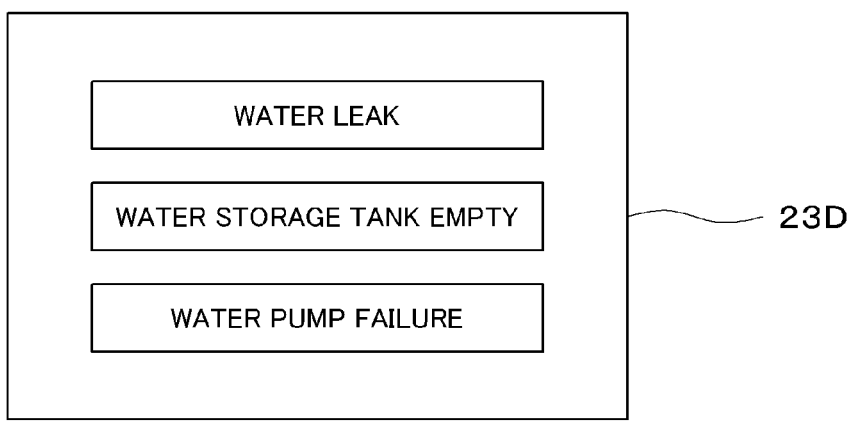
FIG. 9(C) is a diagram showing an indicator of the dialysate feeding device according to the invention.
Figure 10:
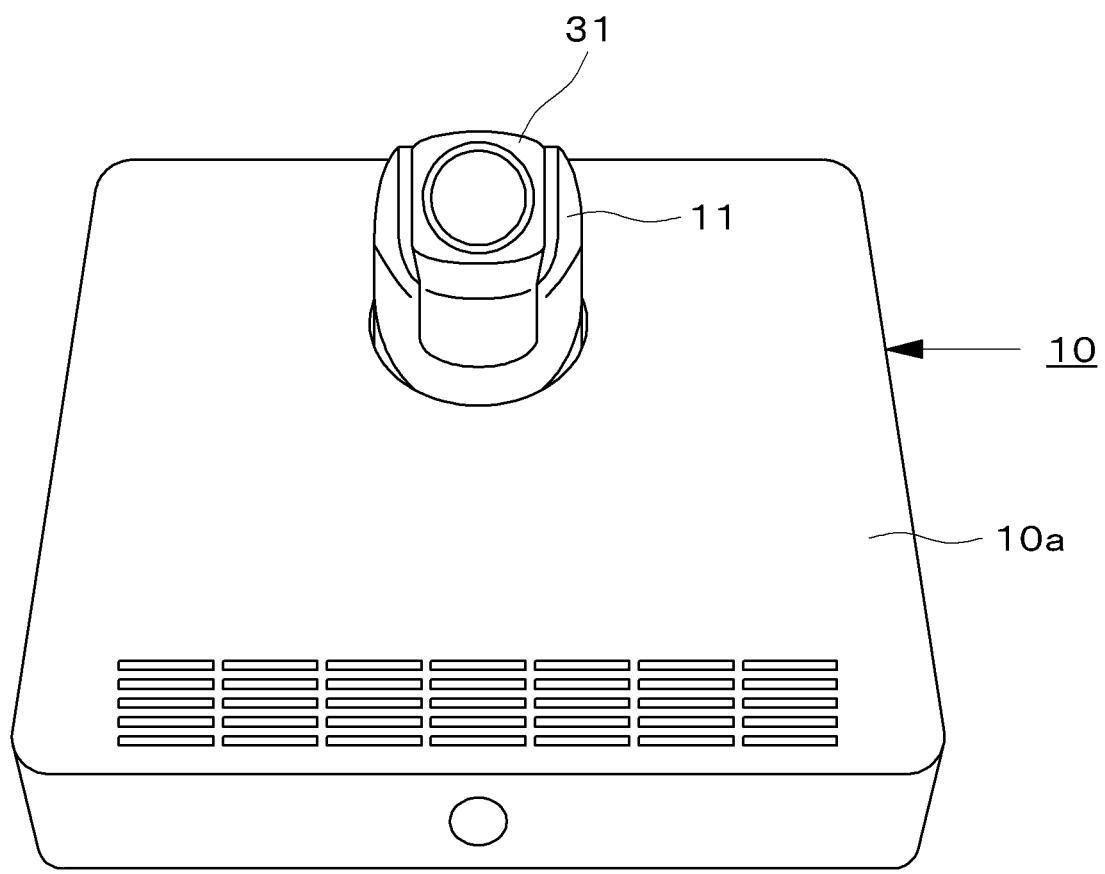
FIG. 10 is a diagram showing an appearance of a monitoring unit.
Figure 11:
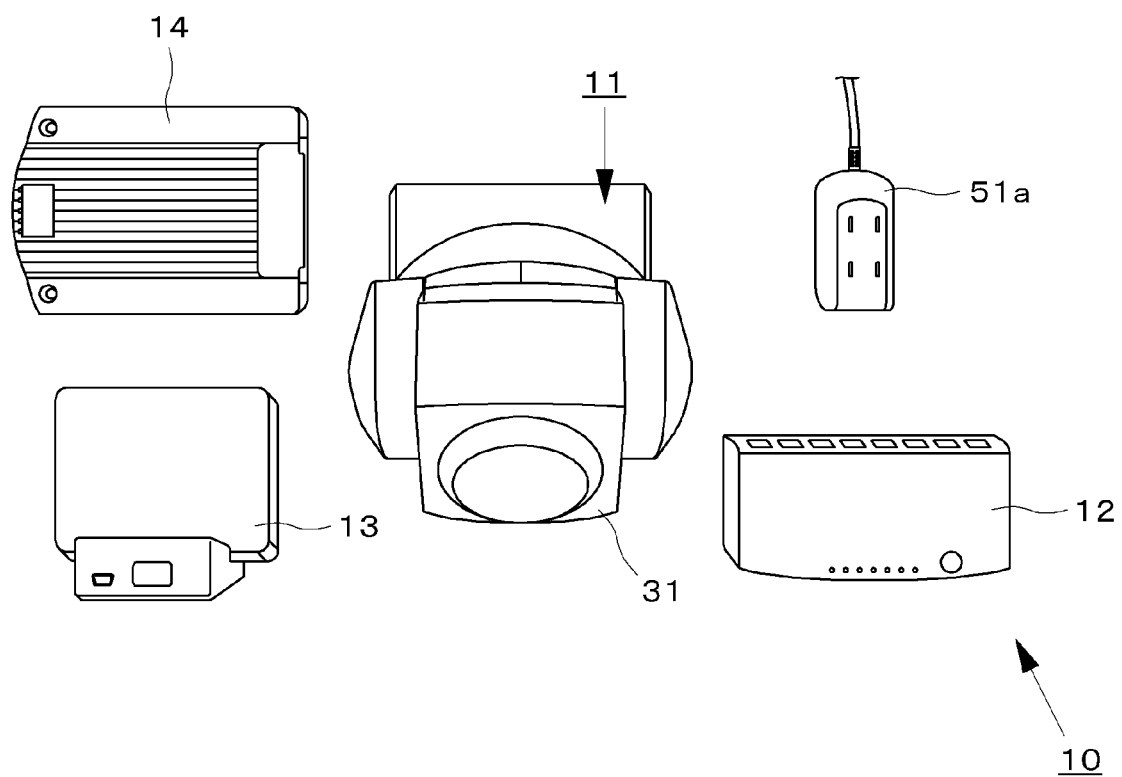
FIG. 11 is a diagram showing components of the monitoring unit.
Figure 13:
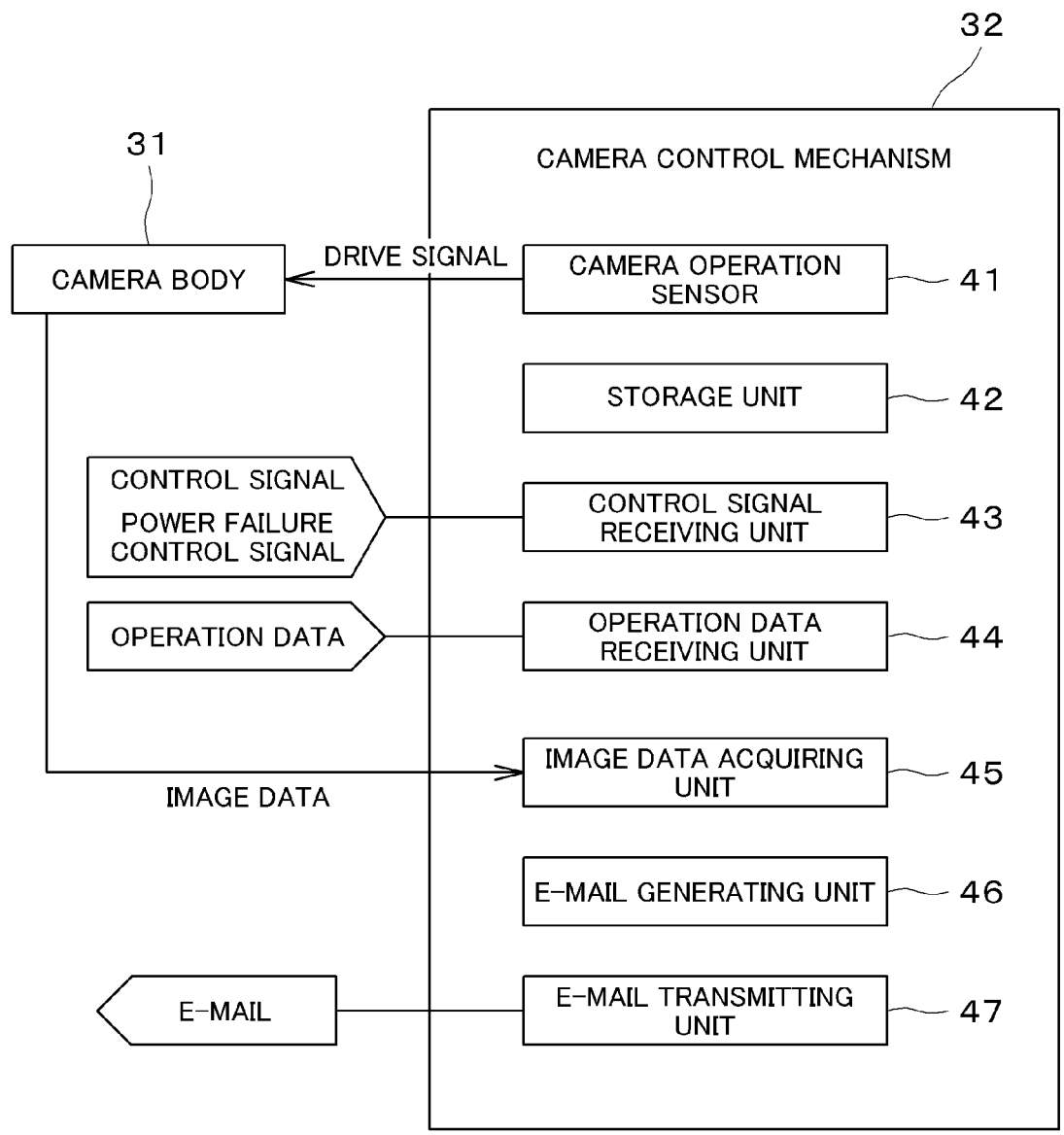
FIG. 13 is a diagram for explaining a configuration of the camera-side control mechanism in a functional aspect.
Figure 14:
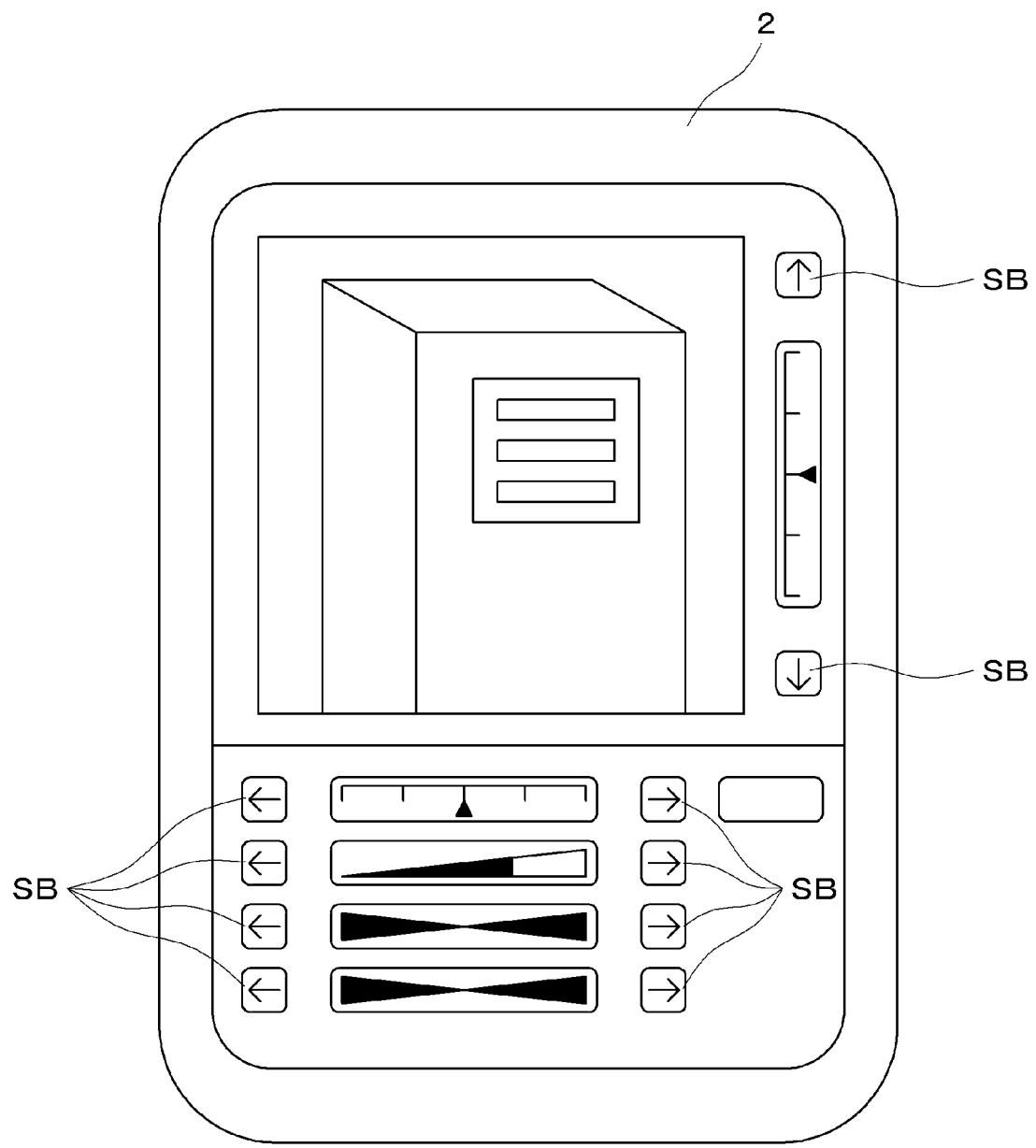
FIG. 14 is a diagram showing an example of a camera operation screen.
Figure 15:
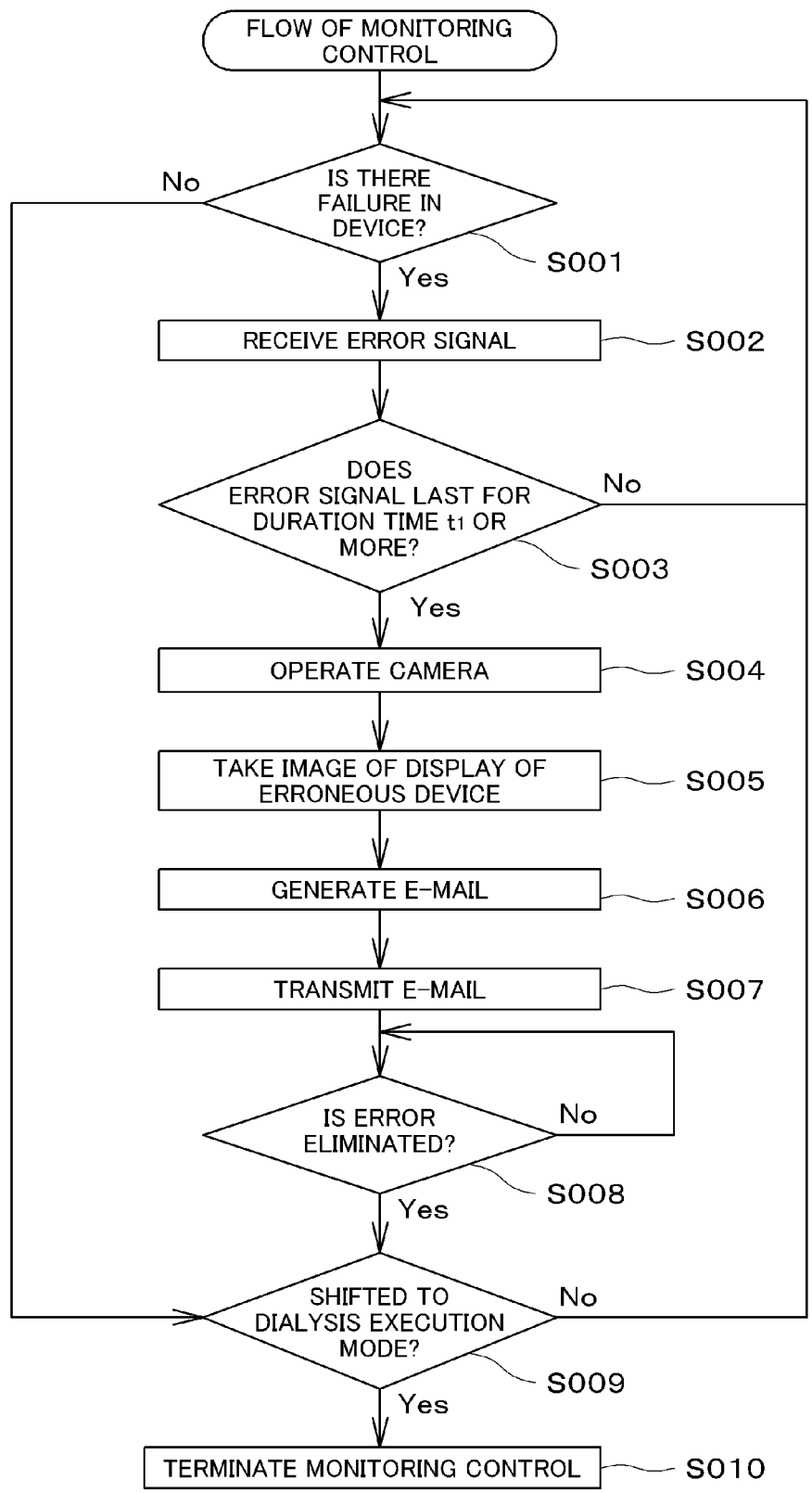
FIG. 15 is a diagram showing a flow of monitoring control by the dialysis treatment instrument monitoring system according to the invention.
Figure 16:
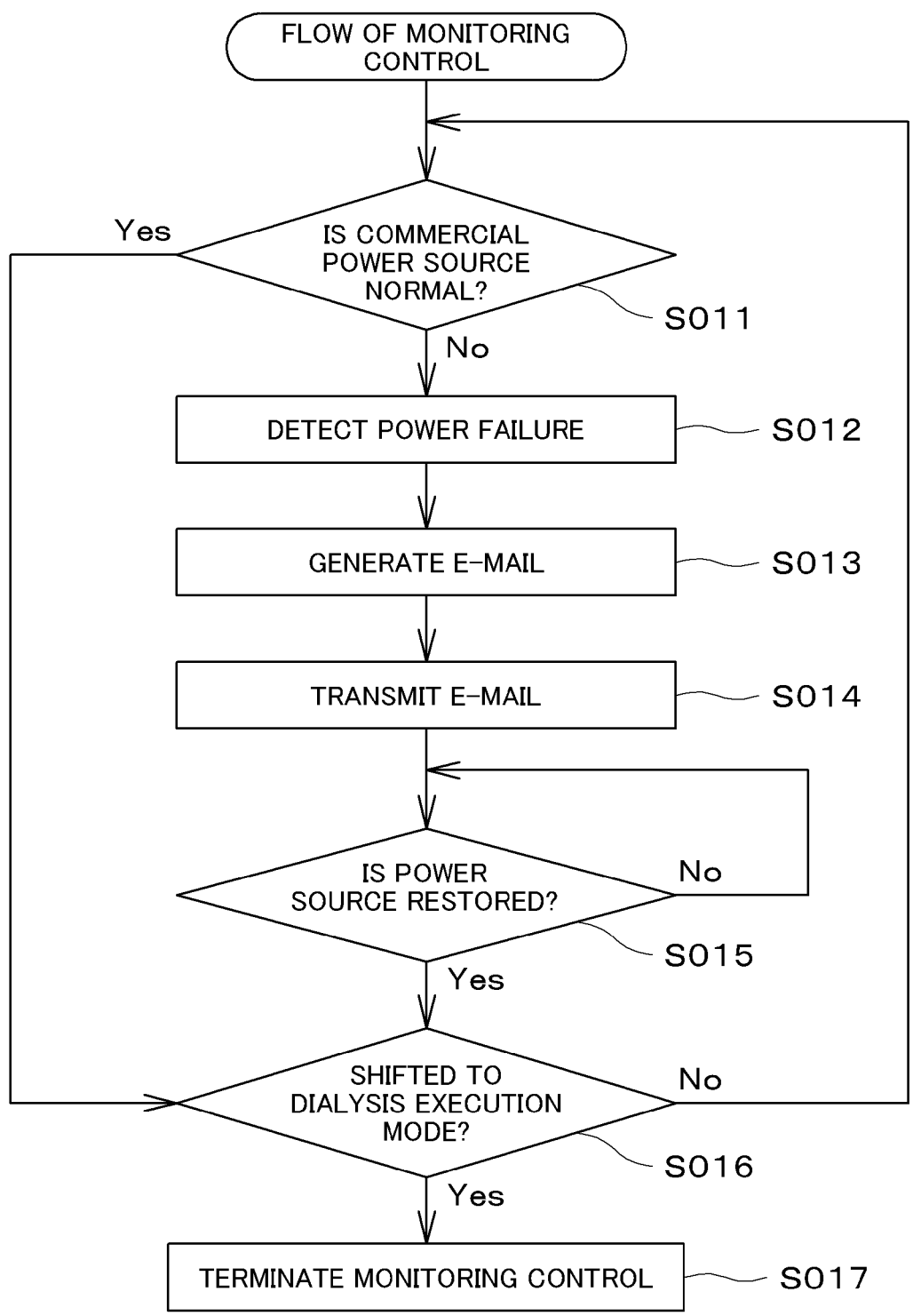
FIG. 16 is a diagram showing a flow of the monitoring control at a time of a power failure.
Figure 17:
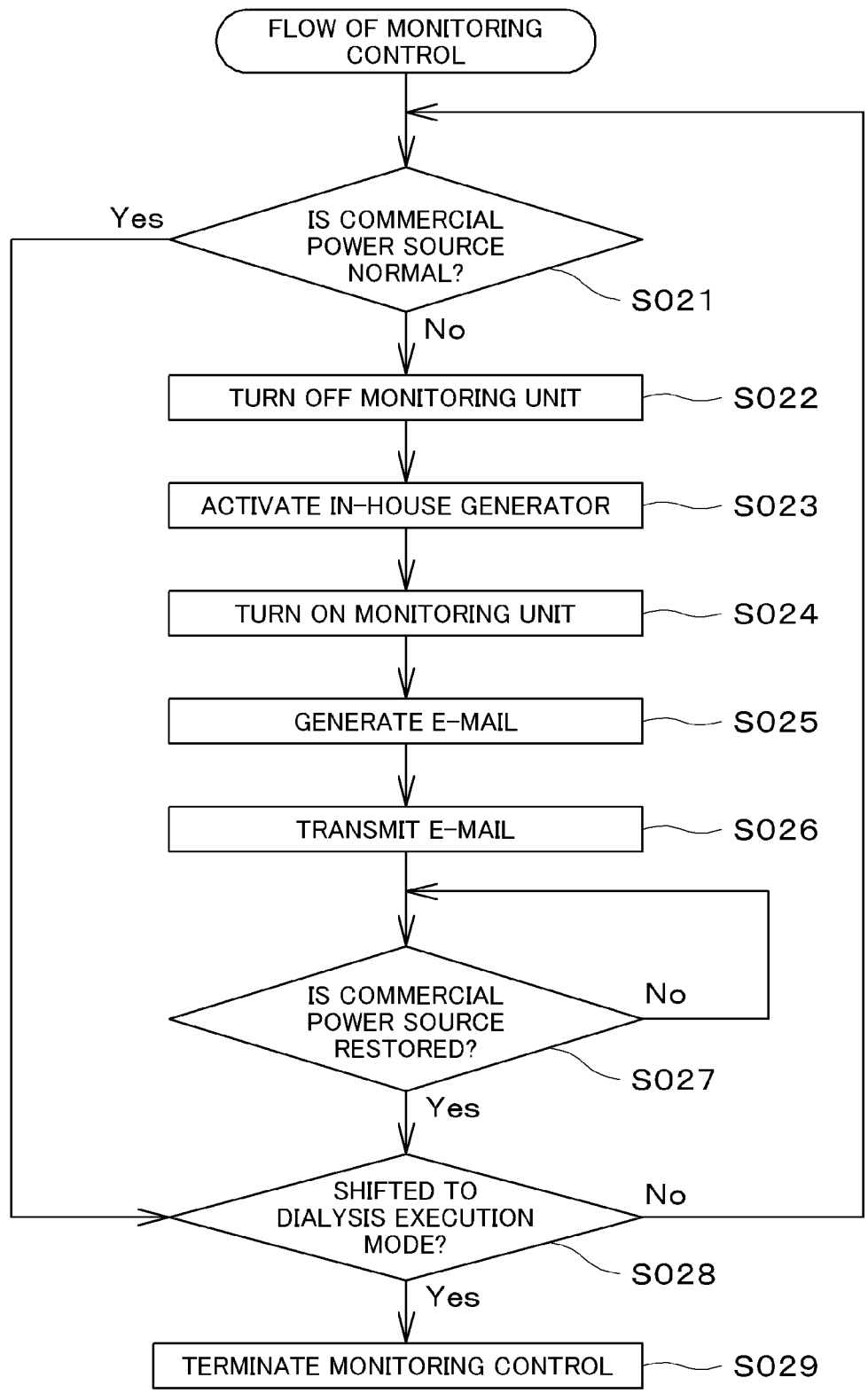
FIG. 17 is a diagram showing a modification of the flow of the monitoring control at the time of power failure.
Figure 18:
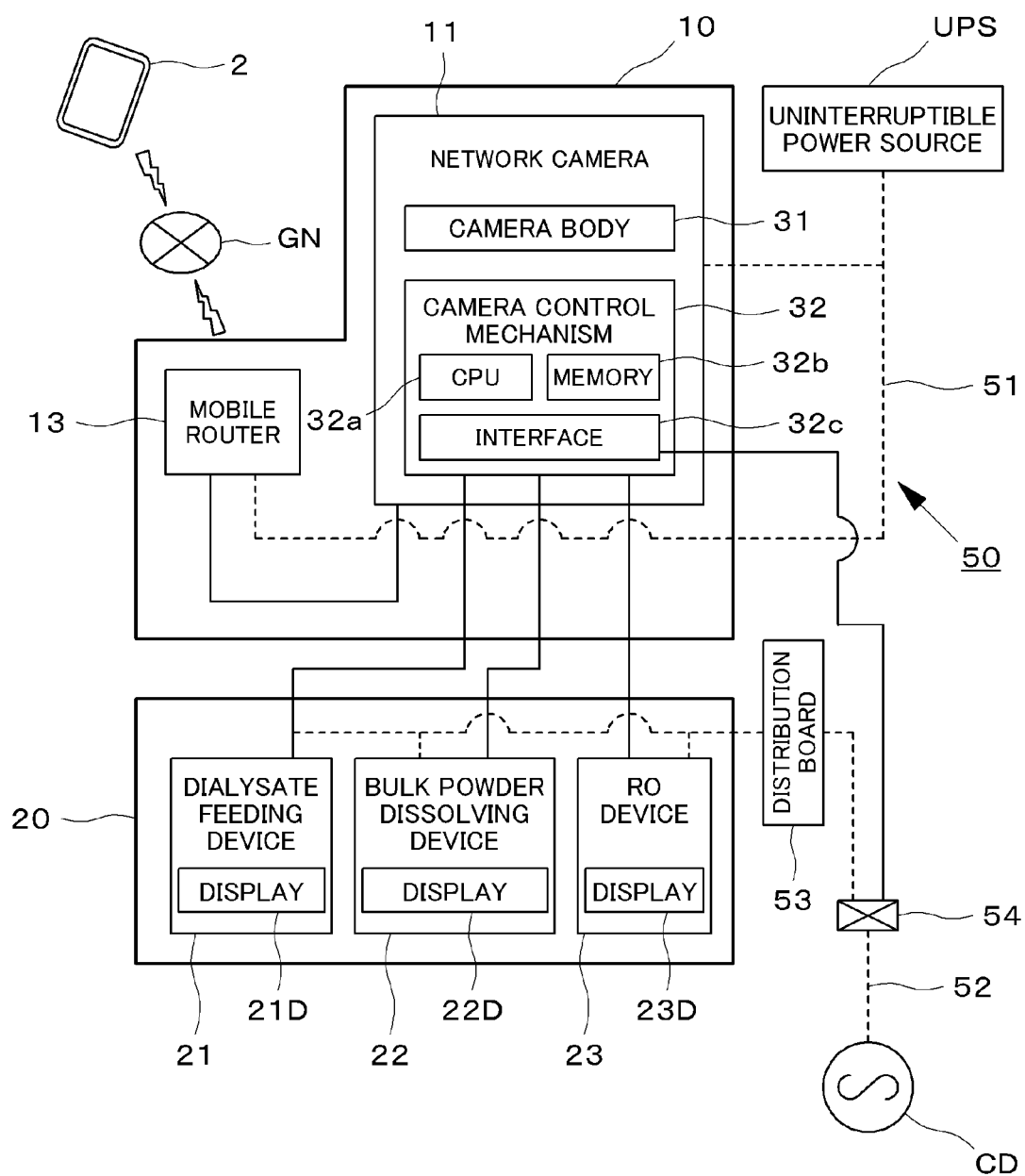
FIG. 18 is a diagram showing a modification of the dialysis treatment instrument monitoring system.

FIG. 1 is a diagram showing a configuration of a dialysis treatment instrument monitoring system according to the present invention. FIG. 2 is a diagram showing a communication network in a facility according to the invention. FIG. 3 is a diagram showing an operation schedule of a dialysis treatment instrument according to the invention. FIG. 4 is a diagram showing an operation content when an operator is absent. FIG. 5 is a conceptual diagram showing a configuration of a refining device according to the invention. FIG. 6 is a conceptual diagram showing a configuration of a dissolving device according to the invention. FIG. 7 is a conceptual diagram showing a configuration of a dialysate feeding device according to the invention. FIG. 8 is a conceptual diagram showing a measuring instrument in the dialysis treatment instrument according to the invention. FIG. 9(A) is a diagram showing an indicator of the refining device according to the invention, FIG. 9(B) is a diagram showing an indicator of the dissolving device according to the invention, and FIG. 9(C) is a diagram showing an indicator of the dialysate feeding device according to the invention. FIG. 10 is a diagram showing an appearance of a monitoring unit to be described later, and FIG. 11 is a diagram showing components of the monitoring unit. FIG. 12 is an explanatory diagram of data stored in a memory of a camera-side control mechanism to be described later, and FIG. 13 is a diagram for explaining a configuration of the camera-side control mechanism in a functional aspect. FIG. 14 is a diagram showing an example of a camera operation screen. FIG. 15 is a diagram showing a flow of monitoring control by the dialysis treatment instrument monitoring system according to the invention. FIG. 16 is a diagram showing a flow of the monitoring control at a time of a power failure. FIG. 17 is a diagram showing a modification of the flow of the monitoring control at the time of power failure. FIG. 18 is a diagram showing a modification of the dialysis treatment instrument monitoring system.

The embodiment to be described later is merely an example for better understanding of the present invention, and not intended to limit the scope of the invention. Of course, the present invention can be altered and modified without departing from the spirit of the invention and also incorporates equivalents thereof.

<<Outline of Dialysis Treatment Instrument Monitoring System According to the Present Invention>>

A dialysis treatment instrument monitoring system 1 according to the present invention (hereinafter, referred to as "the present system") will be outlined with reference to FIGS. 1 to 4. As an example of a facility in which the dialysis treatment instrument is used, a hospital H is used in an explanation below. It should be noted, however, that the hospital H is merely an example of the facility, and that the present system 1 can be used in any other facility in which the dialysis treatment instrument is used, including a doctor's office, a medical office, a clinic, and other medical facilities.

The present system 1 is configured to monitor each of a plurality of dialysis treatment instruments operable to perform a dialysis treatment on a patient in the hospital H during a time period when an operator (hereinafter, also referred to as "the staff") of the dialysis treatment instrument is absent in the hospital H. More specifically, the present system 1 is configured to monitor each of the plurality of dialysis treatment instruments operable to perform the dialysis treatment on the patient during nighttime out of business hours of the hospital H.

The present system 1 includes a monitoring unit 10 shown in FIG. 1 as a main component, and monitors the operating condition of each dialysis treatment instrument configuring a dialysis unit 20 using the monitoring unit 10. More specifically explaining, in the embodiment, a network camera 11 is installed in the hospital H (hereinafter, also referred to merely as "in the hospital"), and the network camera 11 images a predetermined location of each dialysis treatment instrument.

The present system 1 can transmit data indicative of the image taken by the network camera 11 to a communication terminal 2 possessed by the staff via an external communication network GN. The external communication network GN means a communication network that is configured outside the hospital H, and corresponds to the Internet in the embodiment. The communication terminal 2 possessed by the staff is a terminal connected to the Internet and located outside the hospital H, which corresponds to a smartphone possessed by the staff in the embodiment.

More comprehensively, as shown in FIG. 3, the business hours of the hospital H is 9:00 to 18:00 on weekdays, and the staff is present in the hospital and an operating mode of the dialysis unit 20 is set to a dialysis execution mode during these hours, namely daytime. In the dialysis execution mode, each of the dialysis treatment instruments being components of the dialysis unit 20 is in a state of being operable to actually perform the dialysis treatment on a patient or in a standby state ready to start the dialysis treatment.

Meanwhile, during the time between 18:00 weekday and 9:00 following business day is out of the business hours of the hospital H, during which, namely during nighttime, the staff is absent in the hospital and the operating mode of the dialysis unit 20 is set to a dialysis preparation mode. In the dialysis preparation mode, each of the components of the dialysis unit 20 performs a predetermined processing (for example, cleaning/sterilizing processing) in preparation for the dialysis treatment on the following business day. During nighttime when such a dialysis preparation processing is performed, the present system 1 performs the monitoring control for the absence of the staff.

More specifically explaining, if any one of the dialysis treatment instruments falls into an abnormal condition and an error occurs during nighttime, the erroneous device issues an alarm as shown in FIG. 4. The network camera 11 then takes an image of a display of the erroneous device issuing the alarm. Here, the display of the dialysis treatment instrument displays a plurality of error content display windows indicative of error contents that can occur, and among the windows, a window corresponding to the existing error is illuminated on the display of the erroneous device. Accordingly, by taking an image of the display of the erroneous device using the network camera 11, the error content occurring to the erroneous device can be confirmed.

After the network camera 11 has taken an image of the display of the erroneous device, the present system 1 transmits an e-mail to which the image data thereof is attached to the smartphone, which is the communication terminal 2 possessed by the staff. When the communication terminal 2 receives the e-mail outside the hospital H, the staff views the image attached to the e-mail to confirm the occurrence of the error and the error content. The staff then remotely controls the network camera 11 through a camera operating function loaded on the communication terminal 2, and watches the live image taken by the network camera 11 on the display screen of the communication terminal 2 to see the state of the erroneous device. Alternatively, the staff returns to the hospital H after watching the image attached to the e-mail to directly confirm the condition of the erroneous device on site.

As described above, the present system 1 monitors the operating condition of each dialysis treatment instrument during nighttime in which the staff is absent in the hospital, and when the operating condition of the dialysis treatment instrument is turned to be in an abnormal condition, the network camera 11 takes an image of the display of the corresponding device and transmits the e-mail to which the taken image is attached to the communication terminal 2. On the staff's side, the smartphone that is the communication terminal 2 receives the e-mail via the Internet serving as the external communication network GN. The e-mail enables the staff, even when he/she is outside the hospital H, to check the image indicated by the transmitted data from the present system 1, thereby understanding the operating condition of the dialysis treatment instrument.

The external communication network GN is not limited to the Internet but may be any communication network configured outside the hospital H, such as a mobile network. Also, the communication terminal 2 is not limited to the smartphone but may be any terminal such as a personal computer or a mobile phone.

Furthermore, in the embodiment, as shown in FIG. 1, the power supply to each dialysis treatment instrument is covered by a commercial power source CD. Therefore, if the commercial power source CD falls into an abnormal condition and the electric power transmission to the hospital H is blocked, i.e. in the case of power failure, the electric power is not supplied to the dialysis treatment instrument, and the dialysis treatment instrument stops accordingly. In the embodiment, if each dialysis treatment instrument stops due to power failure during nighttime, an e-mail indicative of the fact is transmitted from the present system 1 to the communication terminal 2.

More specifically, in the embodiment, as described above, the electric power from the commercial power source CD is received by electric power receiving facilities (not shown) in the hospital, and supplied to each dialysis treatment instrument via a distribution board 53. In the hospital, an electric power supply circuit 52 formed by electric wiring is formed to supply the electric power from the commercial power source CD. In the electric power supply circuit 52, a power failure detection relay 54 is set between the electric power receiving facilities and the distribution board 53, and the power failure detection relay 54 is operable to break the electric power supply circuit 52 when the power supply from the commercial power source CD to the hospital H stops due to power failure.

Meanwhile, the electric power supply to each section of the monitoring unit 10 is covered by an uninterruptible power source UPS provided in the hospital. Thus, in the embodiment, even when the power supply from the commercial power source CD is interrupted to cause power failure, it is possible to continue the electric power supply to each section of the monitoring unit 10. When the electric power supply from the commercial power source CD is interrupted to cause power failure and then the power failure detection relay 54 is activated, which becomes a trigger, each section of the monitoring unit 10 is operated to transmit the e-mail indicative of power failure to the communication terminal 2.

As described above, if power failure occurs during nighttime and each dialysis treatment instrument stops its operation, the present system 1 transmits the e-mail indicative of the event to the communication terminal 2. On the staff side, the communication terminal 2 receives the e-mail via the Internet serving as the external communication network GN. This e-mail enables the staff to understand that each of the dialysis treatment instruments stopped due to power failure.

While the monitoring unit 10 constructs a communication network in the hospital, there is another communication network configured by terminals (hereinafter, intrahospital terminals) 101 other than the monitoring unit 10 in the hospital. Specifically, as shown in FIG. 2, the monitoring unit 10 configures a camera network Na as a communication network centering on the network camera 11 in the hospital. Meanwhile, a plurality of intrahospital terminals 101 are provided in the hospital for managing a medical instrument, a diagnostic instrument, or a measuring instrument in the hospital, and the plurality of intrahospital terminals 101 configure the intrahospital network Nb as the communication network via a switching HUB 102.

In the embodiment, the camera network Na and the intrahospital network Nb are independent of each other in an isolated state. Furthermore, each of the camera network Na and the intrahospital network Nb includes a separate router 13, 103 capable of establishing connection with the Internet independently. In this manner, for example, the intrahospital network Nb is not affected when the data of the image taken by the network camera 11 is transmitted to the communication terminal 2, and similarly the camera network Na is not affected when the intrahospital terminal 101 communicates with a terminal on the Internet. This configuration will be described later in detail.

<<Configuration of Dialysis Treatment Instrument Monitoring System According to the Present Invention and Peripheral Devices>>

Next, a configuration of the present system 1 and each of the peripheral devices will be explained. As shown in FIG. 1, the monitoring unit 10 serving as the main component of the present system 1 and the dialysis unit 20 to be monitored thereby are arranged in the hospital. Furthermore, an electric power supply unit 50 supplying the electric power to each section of the monitoring unit 10 and the dialysis unit 20 is provided in the hospital.

The configuration of each unit will be described below in the order of the dialysis unit 20, the monitoring unit 10, and the electric power supply unit 50.

(1) Dialysis Unit

A configuration of the dialysis unit 20 will be explained with reference to FIGS. 5 to 9.

The dialysis unit 20 is constituted by the plurality of dialysis treatment instruments operable to perform the dialysis treatment on a patient in the hospital, and the dialysis unit 20 includes, in the embodiment, three types of devices. Specifically explaining, in the embodiment, the dialysis unit 20 includes a dialysate feeding device 21, a bulk powder dissolving device 22 as a dissolving device, and a reverse osmosis membrane device (hereinafter, "RO device") 23 as a refining device.

The RO device 23 refines raw water including city water and well water using a reverse osmosis membrane, and includes, as shown in FIG. 5, a water storage tank 61 that stores therein the raw water, a reverse osmosis membrane module (indicated as RO module in FIG. 5) 62 that refines the raw water, and a water pump 63 that pumps the raw water from the water tank 61 to the reverse osmosis membrane module 62. Refined water obtained by the RO device 23 refining the raw water is used when the bulk powder dissolving device 22 dissolves the bulk powder of the dialysate, when the dialysate feeding device 21 mixes undiluted dialysate therewith to deliver the dialysate, and when the inside of the bulk powder dissolving device 22 and the dialysate feeding device 21 are cleaned.

The bulk powder dissolving device 22 dissolves bulk powder of the dialysate and according to the embodiment, dissolves two types of bulk powder, i.e., agent A bulk powder and agent B bulk powder. For this purpose, in the embodiment, as shown in FIG. 6, the bulk powder dissolving device 22 includes an agent A bulk powder dissolution bath 64 for dissolving the agent A bulk powder therein and an agent B bulk powder dissolution bath 65 for dissolving the agent B bulk powder therein, for dissolving the corresponding bulk powder in the dissolution baths 64, 65, respectively. According to the embodiment, agent A as undiluted dialysate is obtained by dissolving the agent A bulk powder, and agent B as undiluted dialysate is obtained by dissolving the agent B bulk powder.

The dialysate feeding device 21 mixes the refined water obtained by the RO device 23 refining the raw water with the agent A and the agent B obtained by the bulk powder dissolving device 22 dissolving the agent A bulk powder and the agent B bulk powder, respectively, and delivers the dialysate. The dialysate feeding device 21 includes, as shown in FIG. 7, tanks 66, 67, 68 for storing therein the refined water, the agent A, and the agent B, respectively, generate the dialysate by mixing these liquids at a predetermined mixing ratio, and reserves the generated dialysate in a dialysate tank 69. The dialysate feeding device 21 then activates a feeding pump 70, when actually performing the dialysis treatment on the patient, to deliver the dialysate in the dialysate tank 69 at a predetermined feeding pressure.

Each of the three dialysis treatment instruments described above is made into a unit, and set in the same room in the hospital in a state where the device body is stored in a casing (not shown). Furthermore, the dialysis treatment instruments are respectively equipped therein with sensors 21A, 22A, 23A for detecting presence of a failure with the operating condition of the corresponding dialysis treatment instrument, such as a temperature sensor, a concentration sensor, and a pressure sensor, and alarm generators 21B, 22B, and 23B generating an alarm, as shown in FIG. 8. Thus, in the dialysis treatment instrument in which the sensor 21A, 22A, 23A detects a failure, the alarm generator 21B, 22B, 23B generates an alarm.

Moreover, the casings of the dialysis treatment instruments are attached with displays 21D, 22D, 23D, respectively. The displays 21D, 22D, 23D are indicators displaying information on the operating condition of the dialysis treatment instruments. Specifically, as described above, each of the displays 21D, 22D, 23D displays a plurality of error content display windows indicative of error contents that can occur to the dialysis treatment instrument.

For example, the display 21D of the dialysate feeding device 21 has a screen as shown in FIG. 9(A), provided with windows of "water-feeding pressure lower limit," "dialysate concentration lower limit," and "reservoir liquid concentration abnormality." The window of "water-feeding pressure lower limit" is illuminated when the feeding pressure for delivering the dialysate using the feeding pump 70 falls below a management value; the window of "Dialysate concentration lower limit" is illuminated when a solute concentration of the delivered dialysate is out of a management range; and the window "reservoir liquid concentration abnormality" is illuminated when the solute concentration of the dialysate in the dialysate tank 69 is out of the management range. The windows described above are merely an example, and other windows indicative of other error contents may be provided.

Furthermore, the display 22D of the bulk powder dissolving device 22 has a screen as shown in FIG. 9(B), provided with windows of "A dissolution bath high temperature," "B dissolution bath high temperature," and "drug solution leak." The window of "A dissolution bath high temperature" is illuminated when the temperature in the agent A bulk powder dissolution bath 64 rises to the management value or higher; the window of "B dissolution bath high temperature" is illuminated when the temperature in the agent B bulk powder dissolution bath 65 rises to the management value or higher; and the window of "drug solution leak" is illuminated when the agent A or the agent B, which are the undiluted dialysate, leaks in the device. The windows described above are merely an example, and other windows indicative of other error contents may be provided.

Moreover, the display 23D of the RO device 23 has a screen as shown in FIG. 9(C), provided with windows of "water leak," "water storage tank empty," and "water pump failure." The window of "water leak" is illuminated when a water leak occurs in the RO device 23; the window of "water storage tank empty" is illuminated when the storage volume of the raw water in the water storage tank 61 falls below the management value; and the window of "water pump failure" is illuminated when the water pump 63 fails. The windows described above are merely an example, and other windows indicative of other error contents may be provided.

The dialysis unit 20 configured as above operates in the dialysis execution mode during daytime when the staff is in the hospital, in which mode the three dialysis treatment instruments cooperate to perform the dialysis treatment on the patient. Although the dialysis unit 20 according to the embodiment is constituted by the dialysate feeding device 21, the bulk powder dissolving device 22, and the RO device 23, any other configuration is acceptable as long as it includes the above three dialysis treatment instruments, and other devices than the above three dialysis treatment instruments may be included.

Meanwhile, the dialysis unit 20 operates in the dialysis preparation mode during nighttime when the staff is absent in the hospital, in which mode the dialysate feeding device 21 and the bulk powder dissolving device 22 perform the dialysis preparation processing of cleaning and sterilizing inside the device, among the three dialysis treatment instruments. Here, the required time for the dialysis preparation processing is set so that the dialysis preparation processing is completed during nighttime; in other words, the dialysis preparation processing is performed during nighttime only for the time period set in advance. In the embodiment, the RO device 23 does not perform the dialysis preparation processing during nighttime, but requires less maintenance of replacing the membrane in accordance with the frequency and time period of use or cleaning the membrane at a frequency of once or twice per week. However, it is not limited to the above maintenance but the RO device 23 may be configured to perform the dialysis preparation processing similar to that of the dialysate feeding device 21 and the bulk powder dissolving device 22 during nighttime.

In the embodiment, each of the dialysate feeding device 21 and the bulk powder dissolving device 22 interrupts the dialysis preparation processing if an error occurs when performing the dialysis preparation processing during nighttime. Furthermore, in the embodiment, the bulk powder dissolving device 22 is configured not to dissolve the bulk powder of the dialysate, namely the agent A bulk powder and the agent B bulk powder, in a state where the dialysis preparation processing has not been completed. The same applies to the dialysate feeding device 21, which means that it does not deliver the dialysate in a state where the dialysis preparation processing has not been completed.

Thus, if an error occurs to the dialysate feeding device 21 or the bulk powder dissolving device 22 in the middle of the dialysis preparation processing, the dialysis preparation processing is interrupted, and therefore the dialysate feeding device 21 and the bulk powder dissolving device 22 cannot perform any processing to execute the dialysis treatment, specifically the bulk powder dissolution processing and the dialysate feeding processing in such a state. That is, if the error occurs to the dialysate feeding device 21 or the bulk powder dissolving device 22 in the middle of the dialysis preparation processing, the dialysis treatment cannot be performed unless the dialysis preparation processing is resumed after resolving the error, or the patient to receive the dialysis treatment will be kept waiting until the dialysis preparation processing is complete after the start of the business hours of the following business day.

Meanwhile, according to the present embodiment, when the operating condition of any dialysis treatment instrument is turned into an abnormal condition during nighttime when the staff is absent in the hospital, as described above, the monitoring unit 10 operates to image the display of the erroneous device and transmits an e-mail to which the image data is attached to the communication terminal 2 via the Internet. Meanwhile, as shown in FIG. 8, the dialysis treatment instruments are equipped therein with error signal output circuits 21C, 22C, 23C, respectively, configured to output an error signal to drive the monitoring unit 10 once the operating condition is turned into an abnormal condition. Here, the error signal means an abnormal signal output from the dialysis treatment instrument of which operating condition is turned into an abnormal condition to be input to an I/O module 14 provided in the monitoring unit 10, which will be described later.

More specifically, the error signal output circuit 21C of the dialysate feeding device 21 outputs the error signal when the error indicated by the error content display window displayed on the display 21D occurs. That is, the dialysate feeding device 21 outputs the error signal when any one error of the error "water-feeding pressure lower limit," the error "dialysate concentration lower limit," and the error "reservoir liquid concentration abnormality" occurred.

Similarly, the bulk powder dissolving device 22 outputs the error signal using the error signal output circuit 22C when any one error of the error "A dissolution bath high temperature," the error "B dissolution bath high temperature," and the error "drug solution leak" occurred. The RO device 23 also output the error signal using the error signal output circuit 23C when any one error of the error "water leak," the error "water storage tank empty," and the error "water pump failure" occurred.

As described above, if the dialysate feeding device 21, the bulk powder dissolving device 22, and the RO device 23 are respectively provided with the items to be monitored assigned thereto and configured to output the error signal in the case where abnormality occurs in each item, it is possible to carefully monitor the operating condition of each of the dialysate feeding device 21, the bulk powder dissolving device 22, and the RO device 23.

The error contents described above are merely an example of the error contents causing the error signal to be output, and the error signal may be output when an error other than those described above occurs as long as the error signal is output at least when the error of the contents described above occurs.

(2) Monitoring Unit

The configuration of the monitoring unit 10 will be explained with reference to FIG. 1 already referenced above as well as FIGS. 10 to 14.

The monitoring unit 10 is made into a unit as shown in FIG. 10, and fixed to a side wall or a ceiling of the same room in the hospital as the room in which dialysis treatment instruments are placed. More specifically, the monitoring unit 10 has a casing 10a formed by plastic, and the casing 10a accommodates therein components of the monitoring unit 10 shown in FIG. 11, specifically the network camera 11, a switching HUB 12, a mobile router 13, and the I/O module 14.

A circular through-hole is formed in the center of the casing 10a and, as shown in FIG. 10, a camera body 31 of the network camera 11 is exposed outside the casing 10a. The casing 10a also accommodates therein, in addition to the components of the monitoring unit 10, a tap 51a forming a part of an electric power supply circuit 51 for supplying electric power from the uninterruptible power source UPS to the components of the monitoring unit 10.

The network camera 11 is a monitoring camera that monitors the operating conditions of the dialysis treatment instruments constituting the dialysis unit 20, specifically the dialysate feeding device 21, the bulk powder dissolving device 22, and the RO device 23. The I/O module 14 is interposed between the network camera 11 and the dialysis treatment instrument to receive the error signal output from the dialysis treatment instrument in an abnormal condition and further to output a control signal to the network camera 11. The mobile router 13 is a relay instrument to connect the camera network Na configured by the monitoring unit 10 to the Internet that is the external communication network GN. The switching HUB 12 mediates data transmission to and from each section of the monitoring unit 10, and functions as a bridge.

A configuration of each section of the monitoring unit 10 will be described below in detail.

The network camera 11 is an IP camera capable of imaging in all directions, and includes the camera body 31 and a camera control unit 32 driving and controlling the camera body 31, as shown in FIG. 1. The camera body 31, corresponding to the imaging device according to the invention, is equipped with a panoramic lens covered by a dome-shaped clear cover, and applicable to panning, tilting, and zooming (pan, tilt, and zoom, hereinafter referred to as "PTZ motion"). More specifically explaining, if the operating condition of any dialysis treatment instrument turns into an abnormal condition during nighttime when the staff is absent in the hospital, the camera body 31 performs the PTZ motion so as to image the display 21D, 22D, 23D of the corresponding device.

The camera control unit 32, corresponding to the control mechanism according to the invention, is configured to control the PTZ motion of the camera body 31 based on data transmitted from an operating terminal operated by a user to adjust the imaging range of the network camera 11 (hereinafter, "operation data").

Specifically, the camera control unit 32 includes, as shown in FIG. 1, a CPU 32a, a memory 32b, and an interface 32c, and the memory 32b stores therein various data and programs. As soon as the interface 32c of the camera control unit 32 receives the operation data via the switching HUB 12, the CPU 32a reads and executes a camera operating program from among the programs stored in the memory 32b. This program identifies an amount of the PTZ motion of the camera body 31 determined by the user on the operating terminal, and causes the camera body 31 to perform the PTZ motion by the identified amount of the motion.

It should be noted that the operating terminal may include the smart phone that is the communication terminal 2 possessed by the staff. Specifically explaining, the application programs installed in the smartphone include the program for remotely controlling the network camera 11, and upon starting the application program, the camera operation screen shown in FIG. 14 is drawn on a touch panel of the smartphone. Through the screen, the staff can remotely control the network camera 11 in the hospital H from the outside of the hospital H. In other words, according to the embodiment, the smartphone possessed by the staff that is the communication terminal 2 is capable of communicating with the network camera 11 via the Internet.

More specifically, the camera operation screen displays a live image taken by the camera body 31 at the present time point and an operation button SB for changing the imaging range of the camera body 31. Here, as the staff presses the operation button SB, operation data corresponding to the button operation is generated by the application program and transmitted to the network camera 11. When the camera control unit 32 of the network camera 11 receives the operation data via the Internet, which becomes a trigger, the camera operating program starts up, the operation data is analyzed by the execution of the program, and consequently the amount of the PTZ motion determined by the staff on the smartphone side is identified.

The camera control unit 32 then causes the camera body 31 to perform the PTZ motion by the identified amount of the PTZ motion. As a result, in response to the type and pressing time of the pressed operation button SB, the imaging range of the camera body 31 is switched and the live image displayed on the camera operation screen is also switched.

Furthermore, the camera control unit 32 can also control the camera body 31 to take an image of the display 21D, 22D, 23D of the device that output the error signal based on the error signal output from the dialysis treatment instrument. Specifically, the error signal output from the dialysis treatment instrument is input to the I/O module 14 and, as soon as the control signal accordingly output from the I/O module 14 is passed to the interface 32c of the camera control unit 32 via the switching HUB 12, the CPU 32a reads out and executes the erroneous device imaging program from the programs stored in the memory 32b. This program is used to cause the camera body 31 to perform the PTZ motion based on the control signal, and through the program being executed, the camera body 31 selectively takes an image of the display 21D, 22D, 23D of the dialysis treatment instrument that has output the error signal.

To explain a specific procedure, the erroneous device imaging program firstly analyzes the control signal received by the interface 32c to identify which dialysis treatment instrument is the erroneous device that output the error signal. Subsequently, the amount of the PTZ motion required by the camera body 31 to image the display 21D, 22D, 23D of the identified dialysis treatment instrument is calculated. The amount of the motion is calculated based on a current imaging position of the camera body 31 and an arranged position of the display 21D, 22D, 23D to be imaged.

Information on the arranged position of the display 21D, 22D, 23D of each dialysis treatment instrument is stored in the memory 32b as preset position information in advance as shown in FIG. 12. After identifying the dialysis treatment instrument that is the erroneous device, the CPU 32a reads out the preset position information corresponding to the identified device from the memory 32b to identify the arranged position of the display 21D, 22D, 23D of the identified device. Meanwhile, the CPU 32a identifies the position that the camera body 31 is currently imaging. The amount of the PTZ motion is calculated based on the two positions identified as above.

As the camera body 31 performs the PTZ motion by the amount of the motion corresponding to the calculation result, the display 21D, 22D, 23D of the erroneous device comes into the imaging range of the camera body 31, and also the display 21D, 22D, 23D can be imaged at a zoom level allowing to identify which window is illuminated among the error content display windows on the corresponding display 21D, 22D, 23D.

As described above, by executing the camera operating program, the camera control unit 32 can control the camera body 31 to selectively image the display 21D, 22D, 23D of the dialysis treatment instrument that output the error signal. Furthermore, according to the embodiment, the camera control unit 32 also functions as a data transmission unit that acquires the image data indicative of the image of the display 21D, 22D, 23D taken by the camera body 31 and transmits the acquired image data by attaching it to an e-mail.

Specifically explaining, after the image of the display 21D, 22D, 23D of the dialysis treatment instrument that is the erroneous device is taken by execution of the camera operating program, the CPU 32a reads and executes an e-mail transmission program from the programs stored in the memory 32b. Upon execution of the program, firstly the image data indicative of the image of the display 21D, 22D, 23D taken by the camera body 31 is transferred from the camera body 31 to the camera control unit 32 and temporarily stored in the memory 32b. Although the type of the image data is assumed as still image data in the embodiment, the type is not limited to the embodiment but may be video data.

Subsequently, the e-mail transmission program executes processing of generating an e-mail to which the image data is attached stored in the memory 32b and transmitting the e-mail to a registered e-mail address. More specifically, the staff that requires e-mail delivery has registered an e-mail address assigned to his/her own communication terminal 2 as an e-mail receiving address in advance, and the registered e-mail address is stored in the memory 32b as shown in FIG. 12. As the e-mail is generated, the CPU 32a executes processing of reading the registered e-mail address stored in the memory 32b and transmitting the e-mail to a registered terminal that is the communication terminal 2 corresponding to the registered e-mail address.

To explain the configuration of the camera control unit 32 described above again in a functional aspect, as shown in FIG. 13, the camera control unit 32 includes a camera operation unit 41, a storage unit 42, a control signal receiving unit 43, an operation data receiving unit 44, an image data acquiring unit 45, an e-mail generating unit 46, and an e-mail transmitting unit 47. Each of these units of the camera control unit 32 is configured by the CPU 32a, the memory 32b, the interface 32c, and various programs stored in the memory 32b of the camera control unit 32.

The camera operation unit 41 generates a drive signal as a signal causing the camera body 31 to do the PTZ motion and outputs the signal to the camera body 31. The storage unit 42 stores therein preposition information indicative of the arranged positions of the displays 21D, 22D, 23D of dialysis treatment instruments and the registered e-mail address indicative of the destination of the e-mail transmitted by the e-mail transmitting unit 47. The storage unit 42 also temporarily stores therein the image data indicative of the image taken by the camera body 31.

The control signal receiving unit 43 receives the control signal output from the I/O module 14 when the error signal output from the dialysis treatment instrument is input to the I/O module 14. The operation data receiving unit 44 receives the operation data transmitted by the operating terminal in accordance with the user operation performed to adjust the imaging range of the network camera 11. The image data acquiring unit 45 acquires the image data indicative of the image taken by the camera body 31 from the camera body 31 and stores the data in the storage unit 42.

The e-mail generating unit 46 generates an e-mail to which the image data is attached acquired from the camera body 31 by the image data acquiring unit 45, in other words, the image data temporarily stored in the storage unit 42. The e-mail transmitting unit 47 transmits the e-mail generated by the e-mail generating unit 46 to the registered terminal that is the communication terminal 2 corresponding to the registered e-mail address.

In the camera control unit 32 configured as above, when the operation data receiving unit 44 receives the operation data, which becomes a trigger, the camera operation unit 41 generates a drive signal based on the operation data. The camera body 31 that received the drive signal then performs the PTZ motion by the amount of the motion corresponding to the user operation input to the operating terminal to adjust the imaging range.

The control signal receiving unit 43 receives the control signal, which becomes a trigger, and the camera operation unit 41 analyzes the control signal, identifies the dialysis treatment instrument that output the error signal, and reads out the preposition information indicative of the arranged positions of the displays 21D, 22D, 23D of the identified dialysis treatment instruments from the storage unit 42. The camera operation unit 41 then generates the drive signal based on the preposition information read from the storage unit 42, and outputs it to the camera body 31. The camera body 31 that received the drive signal then performs the PTZ motion so that the display 21D, 22D, 23D of the dialysis treatment instrument that output the error signal comes into the imaging range.

When the camera body 31 subsequently takes an image of the display 21D, 22D, 23D of the dialysis treatment instrument that output the error signal, the image data acquiring unit 45 acquires the image data indicative of the image from the camera body 31. The acquired image data is temporarily stored in the storage unit 42.

When the image data is stored in the storage unit 42, which becomes a trigger, the e-mail generating unit 46 generates an e-mail to which the image data is attached. After generating the e-mail, the e-mail transmitting unit 47 reads the registered e-mail address from the storage unit 42, and transmits the e-mail to the registered terminal corresponding to the registered e-mail address.

After transmitting the e-mail, the image data stored in the storage unit 42 is deleted, and instead, e-mail transmission history data indicative of time and date at which the e-mail was transmitted is stored in the storage unit 42. According to the embodiment, when the control signal receiving unit 43 receives the control signal, control signal reception history data indicative of the time and date of the receipt is stored in the storage unit 42. The time and date indicated by the control signal reception history data can be considered as the time and date at which the dialysis treatment instrument in an abnormal condition output the error signal, i.e. the time and date at which the error occurred to the dialysis treatment instrument.

The switching HUB 12 functions as a bridge, as described above, and passes data to an appropriate destination in accordance with the type of the data. Specifically, the switching HUB 12 is connected to the network camera 11, the mobile router 13, and the I/O module 14 by wired connection to receive the control signal output from an output port of the I/O module 14 and pass it to the network camera 11. The switching HUB 12 also receives the e-mail output from the network camera and the image data attached to the e-mail, and passes them to the mobile router 13. Furthermore, the switching HUB 12 receives the operation data transmitted by the operating terminal for adjusting the imaging range of the network camera 11 through the Internet and the mobile router 13, and passes it to the network camera 11.

The mobile router 13 is equipped therein with a modulator-demodulator, and connected to the Internet as the external communication network GN via a mobile communication line, which is an example of the wireless communication line. Especially the mobile router 13 according to the embodiment is a Wi-Fi (registered trademark) router connected to the Internet via the 3G line which is portable and which can wirelessly connect a wireless-LAN enabled device to the Internet in an environment in which radio wave is available.

According to the embodiment, the camera control unit 32 as the data transmission unit transmits the image data indicative of the image of the display 21D, 22D, 23D taken by the camera body 31 to the registered terminal corresponding to the registered e-mail address through the mobile router 13 (more precisely, the mobile router 13 and the switching HUB 12). The camera control unit 32 also receives the operation data transmitted by the operating terminal for adjusting the imaging range of the network camera 11 through the mobile router 13 (more precisely, the mobile router 13 and the switching HUB 12).

As described above, according to the embodiment, the data transmission between the external communication network GN and the camera network Na is relayed by the mobile router 13. That is, the present system 1 is configured to wirelessly perform the data transmission between the external communication network GN and the camera network Na.

Here, the mobile router 13 is provided in the hospital as a relay instrument dedicated to the present system 1. In other words, the mobile router 13 as the device relaying between the camera network Na and the Internet is provided separately from the router 103 that relays between the intrahospital network Nb configured by a plurality of intrahospital terminals 101 and the Internet. Furthermore, because the mobile router 13 is connected to the Internet via the wireless communication line, there is no need of sharing a communication cable used by the router 103 on the intrahospital network Nb side to connect to the Internet. This allows the camera network Na and the intrahospital network Nb to connect to the Internet independently without affecting each other.

As described above, because the camera network Na and the intrahospital network Nb can be connected to the Internet independently from each other, the present system 1 can communicate with the communication terminal 2 on the Internet without using a facility of the intrahospital network Nb. That is, while the communication is established between the present system 1 and the communication terminal 2, the security of the intrahospital network Nb is not affected. As a result, the security of the intrahospital network Nb is guaranteed.

Furthermore, when the camera network Na is configured, the camera network Na can be configured alone because the facility of the intrahospital network Nb is not used. Thus, the time and effort is not required for investigating the infrastructure of the intrahospital network Nb before introduction of the present system 1 using the camera network Na, thereby reducing the cost of introduction of the present system 1.

Moreover, according to the embodiment as described above, each of the dialysate feeding device 21 and the bulk powder dissolving device 22 is configured to interrupt the dialysis preparation processing upon output of the error signal while performing the dialysis preparation processing during nighttime in this the staff is absent in the hospital. In a state where the dialysis preparation processing is not completed, the bulk powder dissolving device 22 is configured not to dissolve the agent A bulk powder or the agent B bulk powder, and the dialysate feeding device 21 is configured not to deliver the dialysate. Under such a restriction, it is more important to monitor the operating condition of the dialysate feeding device 21 and the bulk powder dissolving device 22 during the time period when the staff is absent in the hospital. Therefore, the embodiment enabling the introduction of the system properly monitoring the operating condition of each dialysis treatment instrument when the staff is absent at a lower cost is more significant.

According to the embodiment, if the error of any content occurs and the error signal is output when each of the dialysate feeding device 21 and the bulk powder dissolving device 22 is performing the dialysis preparation processing, the dialysis preparation processing is interrupted. However, the invention is not limited to the embodiment, but the dialysis preparation processing may be interrupted only when an especially severe error occurs among the error contents.

According to the embodiment, the global IP address assigned to the mobile router 13 to identify the mobile router 13 is the static global IP address. This enables a more reliable communication when the terminal on the Internet communicates with the network camera 11 via the mobile router 13. For example, when the operation data is transmitted from the operating terminal to the network camera 11 for adjusting the imaging range of the network camera 11, the communication is made via the mobile router 13, and if the global IP address of the mobile router 13 is a static global IP address, the operation data can be transmitted to the network camera 11 more reliably.

The global IP address assigned to the mobile router 13 is not limited to the static global IP address and may be dynamic; however, the static global IP address is more desirable in that it enables more reliable communication when communicating each unit of the present system 1 via the mobile router 13.

Furthermore, according to the embodiment, as described above, the image data indicative of the image of the display 21D, 22D, 23D of the dialysis treatment instrument that output the error signal is attached to an e-mail, and the e-mail is transmitted to the terminal corresponding to the registered e-mail address via the mobile router 13 connected to the Internet through the mobile communication line. Thus, by transmitting the e-mail to which the image data is attached via the mobile router, it is possible to inform the staff of abnormality of the dialysis treatment instrument by e-mail, which is universal means, without affecting the intrahospital network Nb. However, the means is not limited to the e-mail as long as the image data can be transmitted wirelessly.

Moreover, according to the embodiment, the mobile router 13 is used as an example of the relay instrument connected to the Internet through the wireless communication line, any other instrument than the mobile router can be used as long as it is connected to the Internet via the wireless communication line, for example, a mobile communication instrument such as a mobile phone having a tethering function.

The I/O module 14 is a contact input/output device, and includes an input port for the error signal output from the dialysis treatment instrument of which operating condition is turned into an abnormal condition, and an output port for the control signal to image the display 21D, 22D, 23D of the dialysis treatment instrument that output the error signal. The input port of the I/O module 14 and an output terminal of the dialysis treatment instrument, and the output port of the I/O module 14 and the input port of the switching HUB 12 are connected with wire, respectively. As the error signal is input to the input port, the control signal is output from the output port to the camera control unit 32 of the network camera 11.

According to the embodiment, the I/O module 14 includes a plurality of input ports and a plurality of output ports. More specifically, the number of the input ports provided to the I/O module 14 is larger than that of the dialysis treatment instrument. In addition, the number of the output ports provided to the I/O module 14 is larger than that of the network camera 11. Thus, the I/O module 14 having an equal to or greater number of input ports than that of the dialysis treatment instrument and an equal to or greater number of output ports than that of the network camera 11 can flexibly deal with the number increase of the dialysis treatment instrument and the network camera 11.

As for the numbers of each of the input ports and the output ports, any number can be set as long as the number of the input ports is larger than that of the dialysis treatment instrument and the number of the output port is larger than that of the network camera 11.

(3) Electric Power Supply Unit

The electric power supply unit 50 supplies electric power to each electric instrument in the hospital, and it is categorized into two systems according to the type of the power source in the embodiment. One system is used to supply electric power transmitted from the commercial power source CD to each electric instrument through the electric power supply circuit 52. According to the embodiment, as described above, the components of the dialysis unit 20, i.e., the dialysate feeding device 21, the bulk powder dissolving device 22, and the RO device 23, are operated by receiving the electric power from the commercial power source CD.

The other system is used to supply electric power from the uninterruptible power source UPS provided in the hospital H. The electric power from the uninterruptible power source UPS is supplied through the electric power supply circuit 51 formed by a cable laid between the uninterruptible power source UPS and the electric instrument. Here, the destination to which the electric power is supplied from the uninterruptible power source UPS is limited to a specific device among the electric instruments in the hospital including, as described above, each section of the monitoring unit 10. That is, according to the embodiment, the network camera 11 (in other words, the camera body 31 and the camera control unit 32), the switching HUB 12, the mobile router 13, and the I/O module 14 are operated by receiving the electric power from the uninterruptible power source UPS.

In the electric power supply circuit 52, the power failure detection relay 54 is provided between the electric power receiving facilities and the distribution board 53, and the power failure detection relay 54 is usually in an on-state and operable to be switched to an off-state when the commercial power source CD falls into an abnormal condition and the electric power transmission from the commercial power source CD stops. Once the power failure detection relay 54 is turned into the off-state, the connection between the commercial power source CD and the electric instrument in the hospital is broken, and the electric power supply to the corresponding electric instrument stops. Furthermore, the power failure detection relay 54 outputs a signal upon turning to the off-state and, as shown in FIG. 1, the signal is input to the I/O module 14.

When the signal from the power failure detection relay 54 is input, the I/O module 14 outputs a power failure control signal to the camera control unit 32 of the network camera 11. The camera control unit 32 that has received power failure control signal generates an alarming e-mail that notifies that the power supply from the commercial power source CD stopped, and transmits it to the registered terminal corresponding to the registered e-mail address stored in the memory 32b via the mobile router 13.

More specifically, when the camera control unit 32 receives power failure control signal, the CPU 32a reads and executes the e-mail transmission program, and the execution of the program triggers generation of the alarming e-mail for notifying that the power supply from the commercial power source CD stopped. The alarming e-mail includes texts indicative of the occurrence of power failure and the time and date of power failure, i.e., the time and date at which the power failure detection relay 54 was turned to the off-state. Subsequently, the e-mail transmission program executes the processing of transmitting the generated e-mail to the registered terminal.

To explain the e-mail transmission procedure described above again in a functional aspect, when the control signal receiving unit 43 receives power failure control signal output from the I/O module 14, which becomes a trigger, the e-mail generating unit 46 generates the alarming e-mail. After generating the e-mail, the e-mail transmitting unit 47 reads the registered e-mail address from the storage unit 42, and transmits the alarming e-mail to the registered terminal corresponding to the registered e-mail address.

Meanwhile, when the control signal receiving unit 43 receives power failure control signal, power failure control signal reception history data indicative of the time and date of its receipt is stored in the storage unit 42. The time and date indicated by power failure control signal reception history data is equated with the time and date at which the power failure detection relay 54 was turned to off-state, i.e. the time and date at which the power supply from the commercial power source CD stopped.

As described above, according to the embodiment, because each section of the monitoring unit 10 is operated by receiving the electric power from the uninterruptible power source UPS, the e-mail notifying that the power supply from the commercial power source CD to the dialysis treatment instrument stopped can be transmitted, and the e-mail delivery allows for notifying the staff outside the hospital H of the occurrence of power failure.

<<Flow of Dialysis Treatment Instrument Monitoring Method According to the Present Embodiment>>

As a dialysis treatment instrument monitoring method according to the embodiment, the dialysis treatment instrument monitoring method using the present system 1 will be described below with reference to FIGS. 15 and 16. In the following explanation, a flow of monitoring control during the time period when the staff is absent in the hospital, namely during nighttime (hereinafter, "monitoring control during the staff's absence") will be mainly explained.

The monitoring control during the staff's absence is initiated by the staff performing an operation for switching the operating mode of the dialysis unit 20 from the dialysis execution mode to the dialysis preparation mode, for example the operation of clicking a mode switching button on an operation screen (not shown), before leaving the hospital. After that, until the mode switching button is clicked again, the monitoring control during the staff's absence is continued.

As shown in FIG. 15, in the monitoring control during the staff's absence, it is monitored whether the operating condition of each of the dialysate feeding device 21, the bulk powder dissolving device 22, and the RO device 23, which are components of the dialysis unit 20, is turned to an abnormal condition (S001). When the operating condition of any dialysis treatment instrument is turned to an abnormal condition, the corresponding dialysis treatment instrument issues an alarm, and among the error content display windows displayed on the display 21D, 22D, 23D of the dialysis treatment instrument, the window corresponding to the error that occurred is illuminated. In the dialysis preparation mode, the dialysate feeding device 21 and the bulk powder dissolving device 22 are performing the dialysis preparation processing, and the one that fell into an abnormal condition of the two devices is configured to stop the dialysis preparation processing.

The erroneous device that is the dialysis treatment instrument in an abnormal condition outputs the error signal (S002). The error signal is input to the I/O module 14 and, as shown in FIG. 15, if the error signal is input continuously for a predetermined time t1 or longer (S003), the I/O module 14 outputs the control signal. The time duration t1 of the error signal serving as a control signal output condition can arbitrarily be set.

The control signal output from the I/O module 14 is passed to the camera control unit 32 of the network camera 11 through the bridge function of the switching HUB 12. When the control signal receiving unit 43 of the camera control unit 32 receives the control signal, which becomes a trigger, the camera operation unit 41 analyzes the control signal to identify the erroneous device, and reads the preposition information indicative of the arranged position of the display 21D, 22D, 23D of the identified erroneous device from the storage unit 42. The camera operation unit 41 then transmits the drive signal to the camera body to operate the camera body 31 based on the preposition information read from the storage unit 42 (S004). The step S004 corresponds to the step at which the camera control unit 32 that is the control mechanism controls the camera body 31 to selectively image any one display 21D, 22D, 23D among the display 21D, 22D, 23D mounted on each dialysis treatment instrument.

The camera body 31 having received the drive signal performs the PTZ motion so that the display 21D, 22D, 23D of the erroneous device comes into the imaging range, and images the corresponding display 21D, 22D, 23D (S005). The step S005 corresponds to the step at which the camera body 31 that is the imaging device images the display 21D, 22D, 23D displaying the information on the operating condition of the dialysis treatment instrument.

Subsequently, the image data of the display 21D, 22D, 23D taken by the camera body 31 is acquired from the camera body by the image data acquiring unit 45, and temporarily stored in the storage unit 42. When the image data is stored in the storage unit 42, which becomes a trigger, the e-mail generating unit 46 of the camera control unit 32 generates an e-mail to which the corresponding image data is attached (S006), and the generated e-mail is transmitted to the registered terminal corresponding to the registered e-mail address stored in the storage unit 42 by the e-mail transmitting unit 47 (S007). Here, the step of acquiring the image data and transmitting the e-mail corresponds to the step at which the camera control unit 32 that is the data transmission unit acquires the image data indicative of the image taken by the camera body 31 from the camera body and transmits the acquired image data.

According to the embodiment, in a state where the mobile router 13 is connected to the Internet via the 3G line, the e-mail is transmitted to the registered terminal on the Internet via the mobile router 13 by the e-mail transmitting unit 47. More specifically explaining, the e-mail transmitted by the e-mail transmitting unit 47 is passed to the mobile router 13 through the bridge function of the switching HUB 12, modulated by the mobile router 13, and then transmitted to the registered terminal on the Internet through the 3G line.

Upon receipt of the e-mail on the registered terminal side, the staff who possesses the corresponding registered terminal opens the image data attached to the e-mail, and checks the image of the display 21D, 22D, 23D of the erroneous device on the display screen of the registered terminal. After that, the staff views the condition of the erroneous device by watching the live image from the network camera by remotely controlling the network camera 11 on the registered terminal, or returning to the hospital H and going to the site where the erroneous device is placed.

When the error is eliminated by the staff taking a measure corresponding to the error content (S008), the alarm of the dialysis treatment instrument that was the erroneous device stops, and the error content display window of the display 21D, 22D, 23D that was illuminated is turned off.

A series of procedures described above is, as shown in FIG. 15, repeated until the operating mode of the dialysis unit 20 shifts to the dialysis execution mode (S009). At the time point of the operating mode of the dialysis unit 20 shifting to the dialysis execution mode, the monitoring control during the staff's absence is completed (S010).

Meanwhile, in the monitoring control while the staff is absent, it is monitored whether the power supply from the commercial power source CD is correct and, when the commercial power source CD falls into an abnormal condition and the power supply from the commercial power source CD stops as shown in FIG. 16 (No at S011), all of the dialysate feeding device 21, the bulk powder dissolving device 22, and the RO device 23 are turned off. The power failure detection relay 54 installed in the electric power supply circuit 52 detects power failure, and it is turned from on-state to off-state (S012). The power failure detection relay 54 in off-state outputs a signal, and the signal is input to the I/O module 14.

When the signal from the power failure detection relay 54 is input to the input port of the I/O module 14, power failure control signal is output from the I/O module 14 to the camera control unit 32 of the network camera 11. When the control signal receiving unit 43 of the camera control unit 32 receives power failure control signal, the e-mail generating unit 46 generates the alarming e-mail notifying the interruption of the power supply from the commercial power source CD (S013). The generated alarming e-mail is transmitted to the registered terminal corresponding to the registered e-mail address stored in the storage unit 42 via the mobile router 13 by the e-mail transmitting unit 47 (S014).

When the alarming e-mail is received by the registered terminal, the staff who possesses the registered terminal confirms the occurrence of power failure and the time and date at which power failure occurred from the texts of the alarming e-mail. After that, when the power supply from the commercial power source CD is restored (S105), the dialysate feeding device 21, the bulk powder dissolving device 22, and the RO device 23 are turned on and resumed.

The above procedures at the time of power failure are also repeated until the operating mode of the dialysis unit 20 shifts to the dialysis execution mode, as shown in FIG. 16 (S016). Then, as described above, at the time point of the operating mode of the dialysis unit 20 shifting to the dialysis execution mode, the monitoring control during the staff's absence is terminated (S016), and power failure countermeasure control described above is terminated accordingly.

Modifications of the Embodiment

As modifications of the embodiment, a first modification that differs from the above embodiment (hereinafter, the subject example) in the form of the power supply and a second modification that differs from the subject example in the configuration of the monitoring unit 10 are described below.

First, the first modification is described with reference to FIG. 17.

In the subject example, as described above, the power supply to the dialysis treatment instruments is covered by the commercial power source CD, and the power supply to each section of the monitoring unit 10 is covered by the uninterruptible power source UPS. Meanwhile, in the first modification, the power supply to the dialysis treatment instruments and each section of the monitoring unit 10 is usually covered by the commercial power source CD, and it is covered by an in-house generator provided in the hospital H if the power supply from the commercial power source CD is interrupted. Thus, the measure taken at the time of power failure in the monitoring control during the staff's absence is different between the first modification and the subject example.

Specifically, as shown in FIG. 17, in the first modification, when the commercial power source CD galls into an abnormal condition in the monitoring control during the staff's absence and the power supply from the commercial power source CD stops (No at S021), each section of the monitoring unit 10 is turned to off-state in addition to the dialysis treatment instruments (S022). Meanwhile, at the time of power failure, the in-house generator is activated (S023), then after taking predetermined period of time for switching operation of the power source, the in-house generator resumes the power supply to the dialysis treatment instruments and the monitoring unit 10. This turns each section of the monitoring unit 10 to on-state and restarts them (S024).

In the first modification, as each section of the monitoring unit 10 restarts, the e-mail generating unit 46 of the camera control unit 32 generates an alarming e-mail notifying that the power source was switched from the commercial power source CD to the in-house generator (S025). The generated alarming e-mail is transmitted to the registered terminal corresponding to the registered e-mail address stored in the storage unit 42 via the mobile router 13 by the e-mail transmitting unit 47 (S026). Upon receipt of the alarming e-mail on the registered terminal side, the staff who possesses the registered terminal confirms from the texts of the alarming e-mail that the power source was switched from the commercial power source CD to the in-house generator.

After that, when the power supply from the commercial power source CD is restored (S027), through the power source switching operation, the power source is switched again from the in-house generator to the commercial power source CD. The procedure above is, as shown in FIG. 17, repeated until the operating mode of the dialysis unit 20 shifts to the dialysis execution mode (S028), and power failure countermeasure control is terminated according to the termination of the monitoring control during the staff's absence (S029).

As described above, in the first modification, after the power supply from the commercial power source CD stops due to power failure, the alarming e-mail notifying that the power supply was resumed by the in-house generator is transmitted. Such a configuration is effective when the in-house generator is provided in the facility such as the hospital H. Meanwhile, the configuration of transmitting the alarming e-mail for notifying that power failure occurred as in the present example is effective when the power to each section of the monitoring unit 10 is supplied by the uninterruptible power source UPS.

Next, the second modification is described with reference to FIG. 18. The monitoring unit 10 according to the second modification differs from the monitoring unit 10 in the subject example, as shown in FIG. 18, in that it does not include the switching HUB 12 and the I/O module 14. That is, in the second modification, each of the dialysate feeding device 21, the bulk powder dissolving device 22, and the RO device 23 is directly connected to the network camera 11 by wire, and the network camera 11 is also directly connected to the mobile router 13. This can reduce the cost required for the introduction of the system by the amount of the switching HUB 12 and the I/O module 14.

Meanwhile, in the second modification, the network camera 11 must have enough input terminals for the dialysate feeding device 21, the bulk powder dissolving device 22, and the RO device 23, and therefore the type of the camera that can be used in the second modification is limited. Furthermore, when a plurality of network cameras 11 are used, each network camera 11 must be connected to each dialysis treatment instrument by wire, which can complicates the wiring. In this regard, the present example is more preferable than the second modification.

Moreover, other modifications than the first modification and the second modification described above can also be conceived. For example, the subject example was explained taking an example of system (i.e. the present system 1) monitoring each of a plurality of dialysis treatment instruments as a plurality of medical instruments. The system according to the subject example can monitor the operating condition of each dialysis treatment instrument during the time period when the staff is absent in the hospital, and especially monitor whether the dialysate feeding device 21 and the bulk powder dissolving device 22 are correctly performing the dialysis preparation processing. However, the plurality of medical instruments are not limited to the dialysis treatment instruments, but they may be medical instruments operable to perform another treatment on the patient. That is, the medical instrument monitoring system and the monitoring method according to the invention can be used for medical instruments for a treatment other than the dialysis treatment.

REFERENCE NUMERALS

1 The present system (dialysis treatment instrument monitoring system)

2 Communication terminal
H Hospital
10 Monitoring unit
10a Casing
11 Network camera
12 Switching HUB
13 Mobile router
14 I/O module
20 Dialysis unit
21 Dialysate feeding device
22 Bulk powder dissolving device (dissolving device)
23 RO device (refining device)
21A, 22A, 23A Sensor
21B, 22B, 23B Alarm generator
21C, 22C, 23C Error signal output circuit
21D, 22D, 23D Display
31 Camera body (imaging device)
32 Camera control unit (data transmission unit)
32a CPU
32b Memory
32c Interface
41 Camera operation unit
42 Storage unit
43 Control signal receiving unit
44 Operation data receiving unit
45 Image data acquiring unit
46 E-mail generating unit
47 E-mail transmitting unit
50 Electric power supply unit
51 Electric power supply circuit
51a Tap
52 Electric power supply circuit
53 Distribution board
54 Power failure detection relay
61 Water storage tank
62 Reverse osmosis membrane module
63 Water pump
64 Agent A bulk powder dissolution bath
65 Agent B bulk powder dissolution bath
66 Refined water tank
67 Agent A tank
68 Agent B tank
69 Dialysate tank
70 Feeding pump
101 Intrahospital terminal
102 Switching HUB
103 Router
GN External communication network
CD Commercial power source
UPS Uninterruptible power source
Na Camera network
Nb Intrahospital network
SB Operation button

The invention claimed is:

1. A dialysis treatment instrument monitoring system comprising:
a dialysis treatment unit comprising:
a refining device having a first indicator, configured to refine raw water with a reverse osmosis membrane,
a dissolving device having a second indicator, configured to dissolve bulk power of dialysate, and
a dialysate feeding device having a third indicator, configured to mix refined water obtained by the refining device with undiluted dialysate obtained by the dissolving device and to deliver the dialysate;
a camera capturing an image of at least one of the first indicator, the second indicator, and the third indicator;
a programmable camera control unit ('camera control unit'), wherein the camera control unit comprises a data transmission unit acquiring image data of the image captured by the camera and transmitting the image data to a relay instrument, the relay instrument configured to receive the image data from the data transmission unit and to transmit via an external communication network the image data to a terminal outside the facility, which facility is connected to the external communication network, wherein the dialysis treatment instrument monitoring system is in a state of isolation from any other communication network configured by other instruments in said facility,
wherein
the first indicator, the second indicator, and the third indicator indicates information about an operating condition of the refining device, the dissolving device, and the dialysate feeding device respectively, wherein the operating condition includes: a condition of a feeding pressure for the dialysate, a solute concentration of the dialysate, a temperature of a dissolution bath in which the bulk powder is dissolved, a condition of a water in the refining device and the undiluted dialysate in the dissolving device, a condition of a water pump pumping the raw water, and a condition of a water storage tank,
the camera control unit stores information about an arranged position of each of the first indicator, the second indicator, and the third indicator in a memory as preset position information in advance, and
the camera control unit is programmed such that:
when the camera control unit identifies one of the refining device, the dissolving device, and the dialysate feeding device, indicating a predetermined condition of the operating condition, as an erroneous device, the camera control unit:
retrieves the preset position information corresponding to the erroneous device from the memory and identifies the arranged position of the first indicator, the second indicator, or the third indicator of the erroneous device;
identifies a capturing position in which the camera is currently capturing;
calculates an amount of a motion of the camera based on the arranged position and the capturing position; and
controls the camera to move by the calculated amount of the motion;
the dissolving device and the dialysate feeding device perform a dialysis preparation process including cleaning and sterilizing inside the devices, and terminate the dialysis preparation process when the operating condition is turned into the predetermined condition during the dialysis preparation process,
the relay instrument is provided as a device dedicated to the dialysis treatment instrument monitoring system in the facility and connected to the external communication network via a wireless communication line,
the refining device, the dissolving device, the dialysate feeding device, the camera, the camera control unit, and the relay instrument are placed in a same room of the facility, and
the relay instrument is provided separately from a router that relays between the external communication network and another communication network configured by a plurality of terminals other than components of the dialysis treatment instrument monitoring system in the facility.

2. The dialysis treatment instrument monitoring system according to claim 1, wherein the dissolving device does not start dissolving the bulk powder in a state where the dialysis preparation process is not completed, and the dialysate feeding device does not start delivering the dialysate in a state where the dialysis preparation process is not completed.

3. The dialysis treatment instrument monitoring system according to claim 2, wherein
the relay instrument is a mobile router connected to the Internet as the external communication network via a mobile communication line, and
the data transmission unit transmits an e-mail to which the image data is attached to a registered terminal that is the terminal corresponding to a registered e-mail address via the mobile router.

4. The dialysis treatment instrument monitoring system according to claim 3, further comprising a network camera equipped with the camera and the camera control unit, wherein
the terminal is capable of communicating with the network camera via the mobile router, and
a global internet protocol address assigned to the mobile router to identify the mobile router is a static global internet protocol address.

5. The dialysis treatment instrument monitoring system according to claim 3, wherein
the data transmission unit and the mobile router operate by receiving electric power from an uninterruptible power source provided in the facility, and
if power supplied from a first power source to the dialysis treatment instrument is interrupted, the data transmission unit transmits an e-mail indicating interruption of the power supply to the registered terminal via the mobile router.

6. The dialysis treatment instrument monitoring system according to claim 5, wherein
each of the refining device, the dissolving device, and the dialysate feeding device has an error signal output circuit and outputs an error signal when the operating condition turns into the predetermined condition, and
the dialysis treatment instrument monitoring system further comprises:
an input/output module having an input port for the error signal output from the error signal output circuit, and an output port for a control signal output to image the indicator of the dialysis treatment instrument that outputs the error signal, wherein the input/output module includes at least an equal to or greater number of input ports than that of the dialysis treatment instruments and at least an equal to or greater number of output ports than that of the camera.

7. The dialysis treatment instrument monitoring system according to claim 6, wherein
the refining device outputs the error signal at least when a water leak occurs in the refining device, when a storage volume in a water storage tank that reserves the raw water is less than or equal to a management value, and when a water pump pumping the raw water is in failure,
the dissolving device outputs the error signal at least when a leak of the undiluted dialysate occurs to the dissolving device and when an internal temperature of a dissolution bath in which the bulk powder is dissolved is greater than or equal to a management value, and
the dialysate feeding device outputs the error signal at least when a feeding pressure for feeding the dialysate is less than or equal to a management value, when a solute concentration of the dialysate is out of a management range, and when the solute concentration of the undiluted dialysate in an undiluted solution tank that reserves the undiluted dialysate is out of a management range.

8. A dialysis treatment instrument monitoring method using a dialysis treatment instrument monitoring system within a facility, the method comprising:
capturing, with a camera, an image of an indicator indicating information about an operating condition of at least one of a refining device having a first indicator, a dissolving device having a second indicator, and a dialysate feeding device having a third indicator, wherein the operating condition includes: a condition of a feeding pressure for the dialysate, a solute concentration of the dialysate, a temperature of a dissolution bath in which the bulk powder is dissolved, a condition of a water in the refining device and the undiluted dialysate in the dissolving device, a condition of a water pump pumping the raw water, and a condition of a water storage tank;
controlling, with a programmed camera control ('camera control unit'), the camera to capture the image of at least one of the first indicator, the second indicator, and the third indicator, wherein the camera control unit comprises a data transmission unit; and
acquiring, with the data transmission unit, image data of the image captured by the camera and transmitting the acquired image data to a relay instrument, and
receiving, with the relay instrument connected to an external communication network, the image data from the data transmission unit and transmitting the image data to a terminal connected to the external communication network and located outside the facility, which facility is connected to the external communication network, wherein the dialysis treatment instrument monitoring system is in a state of isolation from any other communication network configured by other instruments in said facility,
wherein
the refining device refines raw water with a reverse osmosis membrane,
the dissolving device dissolves bulk powder of dialysate, and
the dialysate feeding device mixes refined water obtained by the refining device with undiluted dialysate obtained by the dissolving device and delivers the dialysate,
the camera control unit stores information about an arranged position of each of the first indicator, the second indicator, and the third indicator in a memory as preset position information in advance,
wherein the camera control unit has been programmed such that:
when the camera control unit identifies any one of the refining device, the dissolving device, and the dialysate feeding device indicating a predetermined condition of the operating condition, as an erroneous device, the camera control unit:
retrieves the preset position information corresponding to the erroneous device from the memory and identifies the arranged position of the first indicator, the second indicator, or the third indicator of the erroneous device;

identifies a capturing position in which the camera is currently capturing;

calculates an amount of a motion of the camera based on the arranged position and the capturing position; and controls the camera to move by the calculated amount of the motion, the dissolving device and the dialysate feeding device perform a dialysis preparation process including cleaning and sterilizing inside the devices, and terminate the dialysis preparation process when the operating condition is turned into the predetermined condition during the dialysis preparation process, the relay instrument is provided as a device dedicated to the dialysis treatment instrument monitoring system in the facility and connected to the external communication network via a wireless communication line, the refining device, the dissolving device, the dialysate feeding device, the camera, the camera control unit, and the relay instrument are placed in a same room of the facility, and the relay instrument is provided separately from a router that relays between the external communication network and another communication network configured by a plurality of terminals other than components of the dialysis treatment instrument monitoring system in the facility.

9. The dialysis treatment instrument monitoring system according to claim 1, wherein the camera control unit controls the camera to capture a panning image, a tilting image, and a zooming image.

10. The dialysis treatment instrument monitoring system according to claim 1, wherein the predetermined condition is at least one of predetermined temperature, predetermined pressure, predetermined concentration, leakage, storage tank empty, and pump failure.

11. The dialysis treatment instrument monitoring method according to claim 8, wherein the predetermined condition is at least one of predetermined temperature, predetermined pressure, predetermined concentration, leakage, storage tank empty, and pump failure.

12. The dialysis treatment instrument monitoring system according to claim 1, wherein the amount of the motion of the camera is an amount required to move the camera to allow one of the first indicator, the second indicator and third indicator of the erroneous device to position within a capturing range of the camera.

* * * * *